(12) United States Patent
Veliss et al.

(10) Patent No.: US 11,129,953 B2
(45) Date of Patent: Sep. 28, 2021

(54) FOAM RESPIRATORY MASK

(71) Applicant: ResMed Pty Ltd, Bella Vista (AU)

(72) Inventors: Lee James Veliss, Rotterdam (NL);
Alicia Kristianne Wells, Sydney (AU);
Fiona Catherine Carroll, Hawkesbury
(AU); Gerard Michael Rummery,
Woodford (AU); **David Anthony
Pidcock**, Sydney (AU)

(73) Assignee: ResMed Pty Ltd, Bella Vista (AU)

( * ) Notice: Subject to any disclaimer, the term of this
patent is extended or adjusted under 35
U.S.C. 154(b) by 225 days.

(21) Appl. No.: 16/022,180

(22) Filed: Jun. 28, 2018

(65) Prior Publication Data

US 2018/0304037 A1      Oct. 25, 2018

Related U.S. Application Data

(63) Continuation of application No. 12/735,977, filed as application No. PCT/AU2009/000240 on Feb. 27, 2009, now abandoned.

(30) Foreign Application Priority Data

Mar. 4, 2008   (AU) ................................ 2008901057

(51) Int. Cl.
*A61M 16/06*        (2006.01)
(52) U.S. Cl.
CPC .... *A61M 16/0683* (2013.01); *A61M 16/0605* (2014.02); *A61M 16/0666* (2013.01); *A61M 16/0611* (2014.02)

(58) Field of Classification Search
CPC ........ A61M 16/00; A61M 16/06–0694; A61M 16/0003–0012; A61M 2016/0015–0042;
(Continued)

(56) References Cited

U.S. PATENT DOCUMENTS 443,191 A    12/1890   Illing
781,516 A     1/1905   Guthrie, Jr.
(Continued)

FOREIGN PATENT DOCUMENTS

AU      199651130      10/1996
AU      2005100738     11/2005
(Continued)

OTHER PUBLICATIONS

U.S. Appl. No. 10/385,701, filed Aug. 2003, Berthon-Jones et al.
(Continued)

*Primary Examiner* — Jan Christopher L Merene
*Assistant Examiner* — Ned T Heffner
(74) *Attorney, Agent, or Firm* — Nixon & Vanderhye P.C.

(57) ABSTRACT

A patient interface for delivering breathable gas to a patient includes a foam interfacing portion adapted to provide a nasal interface to contact under and around the patient's nose in use and including an orifice adapted to surround both the patient's nares in use, and a positioning and stabilizing structure to support the foam interfacing portion in an operative position on the patient's face. The positioning and stabilizing structure is structured to provide a range of rotational, axial, and/or lateral movement to the foam interfacing portion while maintaining a sufficient interface and resisting the application of tube drag and/or headgear tension to the foam interfacing portion.

35 Claims, 25 Drawing Sheets

(58) Field of Classification Search
CPC .... A62B 7/00; A62B 7/04; A62B 7/14; A62B 18/00; A62B 18/10; B63C 11/12; B63C 11/18

See application file for complete search history.

(56) References Cited

U.S. PATENT DOCUMENTS

| | | |
|---|---|---|
| 1,081,745 A | 12/1913 | Johnston |
| 1,125,542 A | 1/1915 | Humphries |
| 1,192,186 A | 7/1916 | Greene |
| 1,229,050 A | 6/1917 | Donald |
| 1,282,527 A | 10/1918 | Bidonde |
| 1,362,766 A | 12/1920 | McGargill |
| 1,445,010 A | 2/1923 | Feinberg |
| 1,610,793 A | 12/1926 | Kaufman |
| 1,873,160 A | 8/1932 | Sturtevant |
| 2,353,643 A | 7/1944 | Bulbulian |
| 2,415,846 A | 2/1947 | Randall |
| 2,433,565 A | 12/1947 | Korman |
| 2,625,155 A | 1/1953 | Engelder |
| 2,706,983 A | 4/1955 | Matheson et al. |
| 2,931,356 A | 4/1960 | Schwarz |
| 3,013,556 A | 12/1961 | Galleher |
| 3,670,726 A | 3/1972 | Mahon et al. |
| 3,682,171 A | 8/1972 | Dali et al. |
| 3,739,774 A | 6/1973 | Gregory |
| 3,754,552 A | 8/1973 | King |
| 3,827,433 A | 8/1974 | Shannon |
| 3,861,385 A | 1/1975 | Carden |
| 3,902,486 A | 9/1975 | Guichard |
| 3,905,361 A | 9/1975 | Hewson et al. |
| 3,938,614 A | 2/1976 | Ahs |
| 3,972,321 A | 8/1976 | Proctor |
| 4,006,744 A | 2/1977 | Steer |
| 4,142,527 A | 3/1979 | Garcia |
| 4,153,051 A | 5/1979 | Shippert |
| 4,156,426 A | 5/1979 | Gold |
| 4,248,218 A | 2/1981 | Fischer |
| 4,263,908 A | 4/1981 | Mizerak |
| 4,264,743 A | 4/1981 | Maruyama et al. |
| 4,267,845 A | 5/1981 | Robertson, Jr. et al. |
| 4,273,124 A | 6/1981 | Zimmerman |
| 4,312,359 A | 1/1982 | Olson |
| 4,367,735 A | 1/1983 | Dali |
| 4,367,816 A | 1/1983 | Wilkes |
| 4,406,283 A | 9/1983 | Bir |
| 4,414,973 A | 11/1983 | Matheson et al. |
| 4,422,456 A | 12/1983 | Teip |
| 4,449,526 A | 5/1984 | Elam |
| 4,455,675 A | 6/1984 | Bose et al. |
| 4,493,614 A | 1/1985 | Chu et al. |
| 4,548,200 A | 10/1985 | Wapner |
| 4,549,542 A | 11/1985 | Chein |
| 4,572,323 A | 2/1986 | Randall |
| 4,587,967 A | 5/1986 | Chu et al. |
| 4,601,465 A | 7/1986 | Roy |
| 4,617,637 A | 11/1986 | Chu et al. |
| 4,630,604 A | 12/1986 | Montesi |
| 4,641,647 A | 2/1987 | Behan |
| 4,660,555 A | 4/1987 | Payton |
| 4,671,271 A | 6/1987 | Bishop et al. |
| 4,676,241 A | 6/1987 | Webb et al. |
| 4,699,139 A | 10/1987 | Marshall et al. |
| 4,706,664 A | 11/1987 | Snook et al. |
| 4,711,636 A | 12/1987 | Bierman |
| 4,713,844 A | 12/1987 | Westgate |
| 4,753,233 A | 6/1988 | Grimes |
| 4,767,411 A | 8/1988 | Edmunds |
| 4,774,946 A | 11/1988 | Ackerman et al. |
| 4,782,832 A | 11/1988 | Trimble et al. |
| 4,790,829 A | 12/1988 | Bowden et al. |
| 4,802,857 A | 2/1989 | Laughlin |
| 4,803,981 A | 2/1989 | Vickery |
| 4,811,730 A | 3/1989 | Milano |
| 4,830,138 A | 5/1989 | Palmaer et al. |
| 4,838,878 A | 6/1989 | Kalt et al. |
| 4,899,740 A | 2/1990 | Napolitano |
| 4,907,584 A | 3/1990 | McGinnis |
| 4,915,105 A | 4/1990 | Lee |
| 4,919,128 A | 4/1990 | Kopala et al. |
| 4,919,654 A | 4/1990 | Kalt |
| 4,944,310 A | 7/1990 | Sullivan |
| 4,945,907 A | 8/1990 | Tayebi |
| 4,960,121 A | 10/1990 | Nelson et al. |
| 4,966,590 A | 10/1990 | Kalt |
| 4,969,880 A | 11/1990 | Zamierowski |
| 4,971,051 A | 11/1990 | Toffolon |
| 4,976,698 A | 12/1990 | Stokley |
| 4,989,599 A | 2/1991 | Carter |
| 4,996,983 A | 3/1991 | Amrhein |
| 5,000,173 A | 3/1991 | Zalkin et al. |
| 5,005,571 A | 4/1991 | Dietz |
| 5,020,163 A | 6/1991 | Aileo et al. |
| 5,022,900 A | 6/1991 | Bar-Yona et al. |
| 5,023,955 A | 6/1991 | Murphy, II et al. |
| 5,025,805 A | 6/1991 | Nutter |
| 5,038,772 A | 8/1991 | Kolbe et al. |
| 5,042,478 A | 8/1991 | Kopala et al. |
| 5,046,491 A | 9/1991 | Derrick |
| 5,074,297 A | 12/1991 | Venegas |
| 5,113,857 A | 5/1992 | Dickerman et al. |
| 5,117,818 A | 6/1992 | Palfy |
| 5,121,745 A | 6/1992 | Israel |
| 5,127,397 A | 7/1992 | Kohnke |
| 5,137,017 A | 8/1992 | Salter |
| 5,138,722 A | 8/1992 | Urella et al. |
| D333,015 S | 2/1993 | Farmer et al. |
| 5,188,101 A | 2/1993 | Tumolo |
| 5,207,665 A | 5/1993 | Davis et al. |
| 5,220,699 A | 6/1993 | Farris |
| 5,243,709 A | 9/1993 | Sheehan et al. |
| 5,243,971 A | 9/1993 | Sullivan et al. |
| 5,245,995 A | 9/1993 | Sullivan et al. |
| 5,261,893 A | 11/1993 | Zamierowski |
| 5,263,939 A | 11/1993 | Wortrich |
| 5,265,592 A | 11/1993 | Beaussant |
| 5,265,595 A | 11/1993 | Rudolph |
| 5,267,557 A | 12/1993 | Her-Mou |
| 5,269,296 A | 12/1993 | Landis |
| 5,271,391 A | 12/1993 | Graves |
| 5,304,146 A | 4/1994 | Johnson et al. |
| 5,299,599 A | 5/1994 | Farmer et al. |
| 5,335,656 A | 8/1994 | Bowe et al. |
| 5,349,949 A | 9/1994 | Schegerin |
| 5,355,878 A | 10/1994 | Griffiths et al. |
| 5,355,893 A | 10/1994 | Mick et al. |
| 5,364,367 A | 11/1994 | Banks et al. |
| 5,372,130 A | 12/1994 | Stem et al. |
| 5,372,388 A | 12/1994 | Gargiulo |
| 5,372,389 A | 12/1994 | Tam et al. |
| 5,372,390 A | 12/1994 | Conway et al. |
| 5,372,391 A | 12/1994 | Bast et al. |
| 5,375,593 A | 12/1994 | Press |
| 5,385,141 A | 1/1995 | Granatiero |
| 5,394,568 A | 3/1995 | Brostrom et al. |
| 5,396,885 A | 3/1995 | Nelson |
| 5,398,676 A | 3/1995 | Press et al. |
| 5,400,776 A | 3/1995 | Bartholomew |
| 5,419,318 A | 5/1995 | Tayebi |
| 5,425,359 A | 6/1995 | Liou |
| 5,429,683 A | 7/1995 | Le Mitouard |
| 5,437,267 A | 8/1995 | Weinstein et al. |
| 5,441,046 A | 8/1995 | Starr et al. |
| 5,462,528 A | 10/1995 | Roewer |
| 5,477,852 A | 12/1995 | Landis et al. |
| 5,488,948 A | 2/1996 | Dubruille et al. |
| 5,509,409 A | 4/1996 | Weatherholt |
| 5,513,634 A | 5/1996 | Jackson |
| 5,513,635 A | 5/1996 | Bedi |
| 5,526,806 A * | 6/1996 | Sansoni ............ A61M 16/0666 128/206.11 |
| 5,533,506 A | 7/1996 | Wood |
| 5,538,000 A | 7/1996 | Rudolph |
| 5,538,001 A | 7/1996 | Bridges |

(56) References Cited

U.S. PATENT DOCUMENTS

| | | | |
|---|---|---|---|
| 5,540,223 A | 7/1996 | Starr et al. | |
| 5,560,354 A | 10/1996 | Berthon-Jones et al. | |
| 5,570,684 A | 11/1996 | Behr | |
| 5,592,938 A | 1/1997 | Scarberry et al. | |
| 5,623,923 A | 4/1997 | Bertheau et al. | |
| 5,647,357 A | 7/1997 | Barnett et al. | |
| 5,653,228 A | 8/1997 | Byrd | |
| 5,655,527 A | 8/1997 | Scarberry et al. | |
| 5,662,101 A | 9/1997 | Ogden et al. | |
| 5,682,881 A | 11/1997 | Winthrop et al. | |
| D293,613 S | 1/1998 | Wingler | |
| 5,704,345 A | 1/1998 | Berthon-Jones et al. | |
| 5,707,342 A | 1/1998 | Tanaka | |
| 5,724,965 A | 3/1998 | Handke et al. | |
| 5,735,272 A | 4/1998 | Dillon et al. | |
| 5,740,799 A | 4/1998 | Nielson | |
| 5,752,511 A | 5/1998 | Simmons et al. | |
| 5,794,619 A | 8/1998 | Edeiman et al. | |
| 5,807,341 A | 9/1998 | Heim | |
| 5,842,469 A | 12/1998 | Rapp et al. | |
| 5,906,203 A | 5/1999 | Klockseth et al. | |
| 5,918,598 A | 7/1999 | Belfer et al. | |
| 5,921,239 A * | 7/1999 | McCall | A61M 16/06 128/205.25 |
| 5,954,049 A | 9/1999 | Foley et al. | |
| 5,975,079 A | 11/1999 | Hellings et al. | |
| 6,012,455 A * | 1/2000 | Goldstein | A61M 16/0488 128/204.18 |
| 6,019,101 A | 1/2000 | Cotner et al. | |
| 6,026,811 A | 2/2000 | Settle | |
| 6,044,844 A | 4/2000 | Kwok et al. | |
| 6,082,360 A | 7/2000 | Rudolph et al. | |
| 6,086,118 A | 7/2000 | McNaughton et al. | |
| 6,095,996 A | 8/2000 | Steer et al. | |
| 6,098,205 A | 8/2000 | Schwartz et al. | |
| 6,109,263 A | 8/2000 | Feuchtgruber | |
| 6,112,746 A | 9/2000 | Kwok et al. | |
| 6,119,693 A | 9/2000 | Kwok et al. | |
| 6,119,694 A * | 9/2000 | Correa | A61M 16/0666 128/207.13 |
| 6,123,071 A | 9/2000 | Berthon-Jones et al. | |
| 6,123,082 A | 9/2000 | Berthon-Jones | |
| 6,139,787 A | 10/2000 | Harrison | |
| 6,152,137 A | 11/2000 | Schwartz et al. | |
| 6,193,914 B1 | 2/2001 | Harrison | |
| 6,196,223 B1 | 3/2001 | Belfer et al. | |
| 6,211,263 B1 | 4/2001 | Cinelli et al. | |
| 6,231,548 B1 | 5/2001 | Bassett | |
| 6,241,930 B1 | 6/2001 | Harrison | |
| 6,258,066 B1 | 7/2001 | Urich | |
| 6,295,366 B1 | 9/2001 | Haller et al. | |
| 6,328,038 B1 | 12/2001 | Kessler et al. | |
| 6,338,340 B1 | 1/2002 | Finch et al. | |
| 6,341,606 B1 | 1/2002 | Bordewick et al. | |
| 6,347,631 B1 | 2/2002 | Hansen et al. | |
| 6,357,441 B1 | 3/2002 | Kwok et al. | |
| 6,358,279 B1 | 3/2002 | Tahi et al. | |
| 6,374,826 B1 | 4/2002 | Gunaratnam et al. | |
| 6,412,487 B1 * | 7/2002 | Gunaratnam | A61M 16/06 128/205.25 |
| 6,412,488 B1 | 7/2002 | Barnett et al. | |
| 6,412,593 B1 | 7/2002 | Jones | |
| 6,412,847 B2 | 7/2002 | De Gaillard | |
| 6,419,660 B1 | 7/2002 | Russo | |
| 6,422,238 B1 | 7/2002 | Lithgow | |
| 6,423,036 B1 | 7/2002 | Van Huizen | |
| 6,431,172 B1 | 8/2002 | Bordewick | |
| 6,434,796 B1 | 8/2002 | Speirs | |
| 6,439,234 B1 | 8/2002 | Curti et al. | |
| 6,448,303 B1 | 9/2002 | Paul | |
| 6,467,482 B1 | 10/2002 | Boussignac | |
| 6,467,483 B1 * | 10/2002 | Kopacko | A61M 16/06 128/205.25 |
| 6,470,887 B1 | 10/2002 | Martinez | |
| 6,478,026 B1 | 11/2002 | Wood | |
| 6,482,178 B1 | 11/2002 | Andrews et al. | |
| 6,491,034 B1 | 12/2002 | Gunaratnam et al. | |
| 6,513,526 B2 | 2/2003 | Kwok et al. | |
| 6,530,373 B1 | 3/2003 | Patron et al. | |
| 6,532,961 B1 | 3/2003 | Kwok et al. | |
| 6,536,435 B1 | 3/2003 | Fecteau et al. | |
| 6,561,188 B1 | 5/2003 | Ellis | |
| 6,561,190 B1 | 5/2003 | Kwok et al. | |
| 6,561,192 B2 | 5/2003 | Palmer | |
| 6,561,193 B1 | 5/2003 | Noble | |
| 6,571,798 B1 | 6/2003 | Thornton | |
| 6,579,267 B2 | 6/2003 | Lynch et al. | |
| 6,581,601 B2 | 6/2003 | Ziaee | |
| 6,581,602 B2 | 6/2003 | Kwok et al. | |
| 6,584,975 B1 | 7/2003 | Taylor | |
| 6,595,214 B1 | 7/2003 | Hecker et al. | |
| 6,595,215 B2 | 7/2003 | Wood | |
| 6,607,516 B2 | 8/2003 | Cinelli et al. | |
| 6,627,289 B1 | 9/2003 | Dilnik et al. | |
| 6,631,718 B1 | 10/2003 | Lovell | |
| 6,634,358 B2 | 10/2003 | Kwok et al. | |
| 6,637,434 B2 | 10/2003 | Noble | |
| 6,644,315 B2 | 11/2003 | Ziaee | |
| 6,655,385 B1 | 12/2003 | Curti et al. | |
| 6,663,600 B2 | 12/2003 | Bierman et al. | |
| 6,669,712 B1 | 12/2003 | Cardoso | |
| D485,905 S | 1/2004 | Moore et al. | |
| 6,679,257 B1 | 1/2004 | Robertson et al. | |
| 6,679,265 B2 | 1/2004 | Strickland et al. | |
| 6,701,927 B2 | 3/2004 | Kwok et al. | |
| 6,710,099 B2 | 3/2004 | Cinelli et al. | |
| 6,766,800 B2 | 7/2004 | Chu et al. | |
| 6,766,817 B2 | 7/2004 | da Silva | |
| 6,776,162 B2 | 8/2004 | Wood | |
| 6,776,163 B2 | 8/2004 | Dougill et al. | |
| 6,789,543 B2 | 9/2004 | Cannon | |
| 6,805,117 B1 | 10/2004 | Ho et al. | |
| 6,807,967 B2 | 10/2004 | Wood | |
| 6,817,362 B2 * | 11/2004 | Gelinas | A62B 18/025 128/206.12 |
| 6,820,617 B2 | 11/2004 | Robertson et al. | |
| 6,823,865 B2 | 11/2004 | Drew et al. | |
| 6,823,869 B2 | 11/2004 | Raje et al. | |
| 6,826,783 B1 | 12/2004 | Grove et al. | |
| 6,834,650 B1 | 12/2004 | Fini | |
| 6,860,270 B2 | 3/2005 | Sniadach | |
| 6,895,965 B2 | 5/2005 | Scarberry et al. | |
| 6,907,882 B2 | 6/2005 | Ging et al. | |
| 6,918,404 B2 | 7/2005 | Dias da Silva | |
| 6,926,004 B2 | 8/2005 | Schumacher | |
| 6,938,620 B2 | 9/2005 | Payne, Jr. | |
| 6,968,844 B2 | 11/2005 | Liland | |
| 6,972,003 B2 | 12/2005 | Bierman et al. | |
| 6,986,352 B2 | 1/2006 | Frater et al. | |
| 6,997,177 B2 | 2/2006 | Wood | |
| 7,011,090 B2 | 3/2006 | Drew et al. | |
| 7,018,362 B2 | 3/2006 | Bierman et al. | |
| 7,052,127 B2 | 5/2006 | Harrison | |
| 7,066,586 B2 | 6/2006 | da Silva | |
| 7,076,282 B2 | 7/2006 | Munro et al. | |
| 7,080,645 B2 | 7/2006 | Genger et al. | |
| 7,101,359 B2 | 9/2006 | Kline et al. | |
| 7,107,989 B2 | 9/2006 | Frater et al. | |
| 7,146,976 B2 | 12/2006 | McKown | |
| 7,152,599 B2 | 12/2006 | Thomas | |
| 7,152,601 B2 | 12/2006 | Barakat et al. | |
| 7,178,525 B2 | 2/2007 | Matula et al. | |
| 7,191,781 B2 | 3/2007 | Wood | |
| 7,207,328 B1 | 4/2007 | Altemus | |
| 7,210,481 B1 | 5/2007 | Lovell et al. | |
| 7,237,551 B2 | 7/2007 | Ho et al. | |
| 7,243,723 B2 | 7/2007 | Surjaatmadja | |
| D550,836 S | 9/2007 | Chandran et al. | |
| D552,733 S | 10/2007 | Criscuolo et al. | |
| 7,285,255 B2 | 10/2007 | Kadlec et al. | |
| 7,302,950 B2 | 12/2007 | Berthon-Jones et al. | |
| 7,318,437 B2 | 1/2008 | Gunaratnam et al. | |

(56) References Cited

U.S. PATENT DOCUMENTS

| | | | |
|---|---|---|---|
| 7,331,348 B1* | 2/2008 | Beevers | A61M 16/0666 128/200.26 |
| 7,523,754 B2 | 4/2009 | Lithgow | |
| 7,658,189 B2 | 2/2010 | Davidson | |
| 2001/0020474 A1 | 9/2001 | Hecker et al. | |
| 2002/0005198 A1 | 1/2002 | Kwok et al. | |
| 2002/0029780 A1 | 3/2002 | Frater et al. | |
| 2002/0046755 A1 | 4/2002 | DeVoss | |
| 2002/0053347 A1 | 5/2002 | Ziaee | |
| 2002/0066452 A1 | 6/2002 | Kessler et al. | |
| 2002/0069872 A1 | 6/2002 | Gradon et al. | |
| 2002/0096178 A1 | 7/2002 | Ziaee | |
| 2002/0124849 A1 | 9/2002 | Billette De Villemeur | |
| 2002/0143296 A1 | 10/2002 | Russo | |
| 2002/0157673 A1 | 10/2002 | Kessler et al. | |
| 2002/0174868 A1 | 11/2002 | Kwok et al. | |
| 2002/0185134 A1 | 12/2002 | Bishop | |
| 2003/0000526 A1 | 1/2003 | Goebel | |
| 2003/0019495 A1 | 1/2003 | Palkon et al. | |
| 2003/0019496 A1 | 1/2003 | Kopacko et al. | |
| 2003/0079749 A1 | 5/2003 | Strickland et al. | |
| 2003/0089373 A1 | 5/2003 | Gradon et al. | |
| 2003/0111080 A1 | 6/2003 | Olsen et al. | |
| 2003/0154980 A1 | 8/2003 | Berthon-Jones et al. | |
| 2003/0168063 A1 | 9/2003 | Gambone et al. | |
| 2003/0196656 A1 | 10/2003 | Moore et al. | |
| 2003/0196658 A1 | 10/2003 | Ging et al. | |
| 2004/0025882 A1 | 2/2004 | Madaus et al. | |
| 2004/0025885 A1 | 2/2004 | Payne, Jr. | |
| 2004/0045551 A1 | 3/2004 | Eaton et al. | |
| 2004/0065328 A1 | 4/2004 | Amarasinghe et al. | |
| 2004/0106891 A1 | 6/2004 | Langan et al. | |
| 2004/0107968 A1 | 6/2004 | Griffiths | |
| 2004/0111104 A1 | 6/2004 | Schein et al. | |
| 2004/0112384 A1 | 6/2004 | Lithgow et al. | |
| 2004/0118406 A1 | 6/2004 | Lithgow et al. | |
| 2004/0127856 A1 | 7/2004 | Johnson | |
| 2004/0211428 A1 | 10/2004 | Jones | |
| 2004/0226564 A1 | 11/2004 | Persson | |
| 2004/0226566 A1 | 11/2004 | Gunaratnam et al. | |
| 2005/0011523 A1 | 1/2005 | Aylsworth et al. | |
| 2005/0028822 A1 | 2/2005 | Sleeper et al. | |
| 2005/0033247 A1 | 2/2005 | Thompson | |
| 2005/0039757 A1 | 2/2005 | Wood | |
| 2005/0051171 A1 | 3/2005 | Booth | |
| 2005/0051176 A1 | 3/2005 | Riggins | |
| 2005/0056286 A1 | 3/2005 | Huddart et al. | |
| 2005/0061326 A1 | 3/2005 | Payne, Jr. | |
| 2005/0066976 A1 | 3/2005 | Wondka | |
| 2005/0101933 A1 | 5/2005 | Marrs et al. | |
| 2005/0150495 A1 | 7/2005 | Rittner et al. | |
| 2005/0155604 A1 | 7/2005 | Ging et al. | |
| 2005/0211252 A1 | 9/2005 | Lang et al. | |
| 2005/0241644 A1 | 11/2005 | Lynch et al. | |
| 2005/0284481 A1 | 12/2005 | Meyer | |
| 2006/0060200 A1 | 3/2006 | Ho et al. | |
| 2006/0081250 A1 | 4/2006 | Bordewick et al. | |
| 2006/0095008 A1 | 5/2006 | Lampropoulos et al. | |
| 2006/0095009 A1 | 5/2006 | Lampropoulos et al. | |
| 2006/0118117 A1 | 6/2006 | Berthon-Jones | |
| 2006/0124131 A1 | 6/2006 | Chandran et al. | |
| 2006/0137690 A1 | 6/2006 | Gunaratnam et al. | |
| 2006/0174887 A1 | 8/2006 | Chandran et al. | |
| 2006/0020514 A1 | 9/2006 | Jones et al. | |
| 2006/0201514 A1* | 9/2006 | Jones | A61M 16/06 128/206.21 |
| 2006/0207597 A1 | 9/2006 | Wright | |
| 2006/0237017 A1 | 10/2006 | Davidson et al. | |
| 2006/0283461 A1 | 12/2006 | Lubke et al. | |
| 2007/0023044 A1 | 2/2007 | Kwok et al. | |
| 2007/0125387 A1 | 6/2007 | Zollinger et al. | |
| 2007/0144525 A1 | 6/2007 | Davidson et al. | |
| 2007/0186930 A1 | 8/2007 | Davidson et al. | |
| 2007/0267017 A1 | 11/2007 | McAuley et al. | |
| 2007/0272249 A1 | 11/2007 | Chandran et al. | |
| 2007/0282272 A1 | 12/2007 | Bannon et al. | |
| 2008/0004573 A1 | 1/2008 | Kaufmann et al. | |
| 2008/0006277 A1 | 1/2008 | Worboys et al. | |
| 2008/0047560 A1 | 2/2008 | Veliss et al. | |
| 2008/0060649 A1 | 3/2008 | Veliss et al. | |
| 2008/0065022 A1 | 3/2008 | Kyvik et al. | |
| 2008/0110469 A1 | 5/2008 | Weinberg | |
| 2008/0200880 A1 | 8/2008 | Kyvik et al. | |
| 2008/0257354 A1 | 10/2008 | Davidson et al. | |
| 2009/0044808 A1 | 2/2009 | Guney et al. | |
| 2010/0000534 A1 | 1/2010 | Kooij et al. | |
| 2010/0018534 A1 | 1/2010 | Veliss et al. | |
| 2011/0000492 A1 | 1/2011 | Veliss et al. | |

FOREIGN PATENT DOCUMENTS

| | | |
|---|---|---|
| DE | 185017 | 5/1907 |
| DE | 30 11 900 | 10/1980 |
| DE | 146 688 | 2/1981 |
| DE | 37 19 009 | 12/1988 |
| DE | 39 27 038 | 2/1991 |
| DE | 297 23 101 | 7/1998 |
| DE | 197 03 526 | 8/1998 |
| DE | 199 44 242 | 3/2001 |
| DE | 10002571 | 7/2001 |
| DE | 102 13 905 | 10/2002 |
| DE | 10 2004 055 433 | 11/2004 |
| EP | 0 288 937 | 11/1988 |
| EP | 0 427 474 | 5/1991 |
| EP | 0 466 960 | 1/1992 |
| EP | 0 303 090 | 4/1992 |
| EP | 0 658 356 | 6/1995 |
| EP | 0 776 679 | 6/1997 |
| EP | 1 099 452 | 5/2001 |
| EP | 1 258 266 | 11/2002 |
| EP | 1 293 227 | 3/2003 |
| EP | 1 481 702 | 12/2004 |
| FR | 2 720 280 | 12/1995 |
| GB | 532214 | 1/1941 |
| GB | 2 176 404 | 12/1986 |
| GB | 2 368 533 | 5/2002 |
| GB | 2 385 533 | 8/2003 |
| JP | 2000-515784 | 11/2000 |
| WO | WO 1982/003548 | 10/1982 |
| WO | WO 1987/001950 | 4/1987 |
| WO | WO 1992/020392 | 11/1992 |
| WO | WO 1992/020395 | 11/1992 |
| WO | WO 1996/028207 | 9/1996 |
| WO | WO 1998/004310 | 2/1998 |
| WO | WO 1998/012965 | 4/1998 |
| WO | WO 1998/023305 | 6/1998 |
| WO | WO 1999/016327 | 4/1999 |
| WO | WO 1999/025410 | 5/1999 |
| WO | WO 1999/043375 | 9/1999 |
| WO | WO 1999/061088 | 12/1999 |
| WO | WO 2000/020072 | 4/2000 |
| WO | WO 2000/038772 | 7/2000 |
| WO | WO 2000/050121 | 8/2000 |
| WO | WO 00/69521 | 11/2000 |
| WO | WO 2000/072905 | 12/2000 |
| WO | WO 2000/074758 | 12/2000 |
| WO | WO 2000/076568 | 12/2000 |
| WO | WO 2000/078384 | 12/2000 |
| WO | WO 2001/062326 | 8/2001 |
| WO | WO 2001/095965 | 12/2001 |
| WO | WO 2001/097892 | 12/2001 |
| WO | WO 2001/097893 | 12/2001 |
| WO | WO 2002/038221 | 5/2002 |
| WO | WO 2002/045784 | 6/2002 |
| WO | WO 2003/090827 | 11/2003 |
| WO | WO 2003/105921 | 12/2003 |
| WO | WO 2004/022146 | 3/2004 |
| WO | WO 2004/041342 | 5/2004 |
| WO | WO 2004/078230 | 9/2004 |
| WO | WO 2005/053781 | 6/2005 |
| WO | WO 2005/063328 | 7/2005 |
| WO | WO 2005/086943 | 9/2005 |
| WO | WO 2005/099801 | 10/2005 |
| WO | WO 2005/110220 | 11/2005 |

(56) References Cited

FOREIGN PATENT DOCUMENTS

| | | |
|---|---|---|
| WO | WO 2005/118040 | 12/2005 |
| WO | PCT/AU2006/000031 | 1/2006 |
| WO | PCT/AU2006/000417 | 3/2006 |
| WO | PCT/AU2006/000770 | 6/2006 |
| WO | WO 2006/069415 | 7/2006 |
| WO | WO 2006/074513 | 7/2006 |
| WO | WO 2006/074516 | 7/2006 |
| WO | WO 2006/099658 | 9/2006 |
| WO | WO 2006/130903 | 12/2006 |
| WO | WO 2007/009182 | 1/2007 |
| WO | WO 2007/016424 | 2/2007 |
| WO | WO 2007/041751 | 4/2007 |
| WO | WO 2007/041786 | 4/2007 |
| WO | WO 2007/048174 | 5/2007 |
| WO | WO 2007/053878 | 5/2007 |
| WO | PCT/AU2007/001936 | 12/2007 |
| WO | WO 2007/143772 | 12/2007 |
| WO | WO 2007/145534 | 12/2007 |
| WO | WO 2008/070929 | 12/2007 |
| WO | WO 2008/011682 | 1/2008 |
| WO | WO 2008/011683 | 1/2008 |
| WO | WO 2008/040050 | 4/2008 |
| WO | WO 2004/073778 | 6/2008 |
| WO | WO 2009/108994 | 9/2009 |
| WO | WO 2009/109004 | 9/2009 |
| WO | WO 2010/028425 | 3/2010 |

OTHER PUBLICATIONS

U.S. Appl. No. 10/533,928, filed Jul. 2005, Berthon-Jones.
U.S. Appl. No. 10/584,711, filed Dec. 2004, Davidson.
U.S. Appl. No. 10/655,622, filed Sep. 2003, Lithgow.
U.S. Appl. No. 10/781,929, filed Jan. 2008, Gunaratnam et al.
U.S. Appl. No. 10/871,929, filed Feb. 2004, Surjaatmadja.
U.S. Appl. No. 11/080,446, filed Jul. 2005, Ging et al.
U.S. Appl. No. 11/447,295, filed Jun. 2006, Lubke et al.
U.S. Appl. No. 11/474,415, filed Jun. 2006, Davidson et al.
U.S. Appl. No. 11/491,016, filed Feb. 2007, Kwok et al.
U.S. Appl. No. 11/703,082, filed Feb. 2007, Davidson.
U.S. Appl. No. 11/878,932, filed Jul. 2007, Veliss et al.
U.S. Appl. No. 11/878,933, filed Jul. 2007, Veliss et al.
U.S. Appl. No. 12/081,696, filed Apr. 2008, Davidson et al.
U.S. Appl. No. 12/085,191, filed May 2008, Kwok et al.
U.S. Appl. No. 12/219,852, filed Jan. 2008, Guney et al.
U.S. Appl. No. 12/309,696, filed Jan. 2009, Kwok et al.
U.S. Appl. No. 12/382,517, filed Mar. 2009, Lithgow.
U.S. Appl. No. 12/448,250, filed Jun. 2009, Veliss et al.
U.S. Appl. No. 12/461,448, filed Aug. 2009, Berthon-Jones.
U.S. Appl. No. 12/478,537, filed Jun. 2009, Kooij et al.
U.S. Appl. No. 12/656,466, filed Jan. 2010, Biener et al.
U.S. Appl. No. 12/700,878, filed Feb. 2010, Davidson et al.
U.S. Appl. No. 60/424,686, filed Nov. 2002, Lithgow.
U.S. Appl. No. 60/483,622, filed Jul. 2003, Kwok et al.
U.S. Appl. No. 60/533,214, filed Dec. 2003, Drew.
U.S. Appl. No. 60/634,802, filed Dec. 2004, Chandran.
U.S. Appl. No. 60/645,672, filed Jan. 2005, Chandran.
U.S. Appl. No. 60/795,615, filed Apr. 2006, Judson et al.
U.S. Appl. No. 60/833,841, filed Jul. 2006, Veliss.
U.S. Appl. No. 60/835,442, filed Aug. 2006, Selvarajan et al.
U.S. Appl. No. 60/852,649, filed Oct. 2006, Selvarajan et al.
U.S. Appl. No. 60/874,968, filed Dec. 2006, Kwok et al.
U.S. Appl. No. 60/907,856, filed Apr. 2007, Davidson et al.
U.S. Appl. No. 60/924,241, filed May 2007, Kwok et al.
U.S. Appl. No. 60/929,393, filed Jun. 2007, Kwok et al.
U.S. Appl. No. 60/935,179, filed Jul. 2007, Guney et al.
U.S. Appl. No. 60/935,336, filed Aug. 2007, Davidson et al.
U.S. Appl. No. 60/996,160, filed Nov. 2007, Guney et al.
U.S. Appl. No. 61/006,409, filed Jan. 2008, Guney et al.
U.S. Appl. No. 61/031,407, filed Feb. 2008, Henry et al.
U.S. Appl. No. 61/064,818, filed Mar. 2008, Guney et al.
U.S. Appl. No. 61/071,512, filed May 2008, Guney et al.
U.S. Appl. No. 61/213,326, filed May 2009, Dravitzki et al.
U.S. Appl. No. 61/222,711, filed Jul. 2009, Dravitzki et al.
U.S. Appl. No. 61/263,175, filed Nov. 2009, Dravitzki et al.
U.S. Appl. No. 61/272,162, filed Aug. 2009, Dravitzki et al.
U.S. Appl. No. 61/272,250, filed Sep. 2009, Dravitzki et al.
International Preliminary Report on Patentability issued in PCT/AU2009/000240 (dated Sep. 7, 2010).
Supplementary European Search Report dated Dec. 18, 2009 in European Application No. 03810331.3.
International Search Report issued in Appln. No. PCT/AU2009/000240 (dated May 21, 2009).
"Ear Loop Face Mask".
Adam J. Singer MD et al. "The Cyanoacrylate Topical Skin Adhesives," American Journal of Emergency Medicine, vol. 26, 2008, pp. 490-496.
Webster's Third New International Dictionary, 1993, Dictionary definition for adjustable, bendable, and mild steel.
ComfortLite™, Respironics, http://comfortlite.respironics.com.
ComfortLite™ 2, Respironics, http://comfortlite2.respironics.com.
"If You Hate CPAP! You Need CPAP Pro®," www.cpappro.com.
Webster's New World Dictionary, Third College Edition 1988, definition for engaged and flexible.
EP Supplementary Search Report issued in EP Application 03793493, dated Dec. 2, 2009.
European Search Report filed on Jul. 27, 2009 in EP Application No. 07784697.0.
European Search Report issued in EP 07845378.4, dated Dec. 1, 2009.
Examination Report filed in New Zealand Application 539836, dated Aug. 25, 2005.
Examiner's Report No. 3 dated Nov. 18, 2009 in New Zealand Application No. 2003275762.
Extended European Search Report dated Mar. 19, 2009 in European Application No. EP 08161249.
Extended European Search Report dated Sep. 3, 2009 in corresponding EP Application No. 09161984.1.
Extended European Search Report. Application No. EP 08154854, dated Nov. 27, 2008.
Fisher and Paykel Col.—Product Family—http://www.fphcare.com/osa/products.asp/.
Hans Rudolph, Inc.—Mask Products—http://www.rudolphkc.com/products.php?category=MASKS.
International Preliminary Report on Patentability for PCT/AU2004/001832, dated Jul. 3, 2006.
International Search Report filed in PCT/AU2005/000803, dated Jun. 30, 2005.
International Search Report filed in PCT/AU2006/000770, dated Aug. 3, 2006.
International Search Report for PCT/AU2007/001052, dated Oct. 9, 2007.
International Search Report for PCT/AU2007/001051, dated Nov. 5, 2007.
International Search Report for PCT/AU2004/001832, dated Mar. 24, 2005.
International Search Report for PCT/AU2007/001936, dated Mar. 4, 2008.
Joel W. Beam, "Tissue Adhesives for Simple Traumatic Lacerations," Journal of Athletic Training, 2008, vol. 43, No. 2, pp. 222-224.
Merriam-Webster Online Dictionary definition of moveable from the 14th century.
Office Action dated Dec. 22, 2009 in European Appln. No. 04802133.1.
Office Action issued in Japanese Application No. 2007-513621 (dated Aug. 24, 2010) with English translation.
ResMed Co.—Mask Products—http://resmed.com/portal/site/ResMedUS/index.jsp?.
Respironics Co.—Mask Family—http://masksfamily.respironics.com/.
Snapp Nasal Interface, Tiara Medical Systems, Inc.—http://www.tiaramed.com/asp_shops/shopdisplayproducts.asp?id=109&cat=SNAPP%2A+Nasal+Interface.

(56) References Cited

OTHER PUBLICATIONS

Subbu Venkatraman et al., "Review Skin Adhesives and Skin Adhesion 1. Transdermal Drug Delivery Systems," Biomaterials, vol. 19, 1998, pp. 1119-1136.
Supplementary European Search Report dated Sep. 8, 2009 in European Appln. No. 04802133.1.
Unsolicited email from Elson Silva, PhD, dated Mar. 28, 2008, "Requesting IDS of U.S. Pat. No. 6,766,817 for patents on fluids moving on porosity by Unsaturated Hydraulic Flow," (email provided in both HTML and plain text format).
International Search Report PCT/AU2003/001163, dated Nov. 4, 2003.
International Search Report PCT/AU2003/001471, dated Feb. 12, 2004.
International Search Report PCT/AU2009/000240, dated May 21, 2009.
International Search Report PCT/AU2009/000262, dated Jun. 9, 2009.
International Search Report PCT/AU2009/001144, dated Dec. 18, 2009.
Office Action issued in European Appln. No. 05746824.1 (dated Mar. 22, 2011).
A Communication pursuant to Article 94(3) EPC dated Apr. 4, 2017, in a corresponding EP Application No. 09 716 773.8 (9 pages).
A Communication Pursuant to Article 94(3) EPC dated Jun. 4, 2018, in a corresponding European Patent Application No. EP 09 716 773.8 (10 pages).

\* cited by examiner

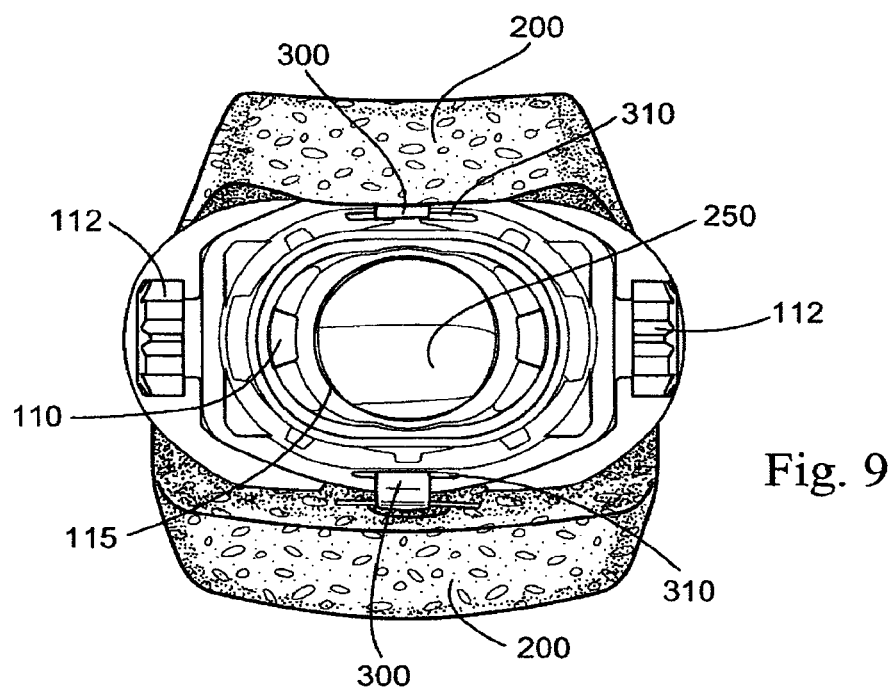
Fig. 9
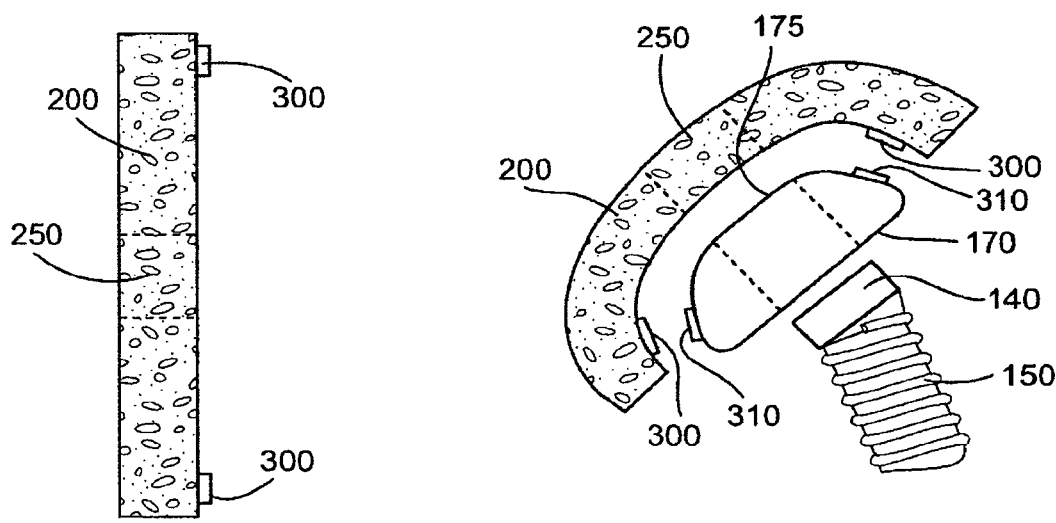
Fig. 10
Fig. 11

FOAM RESPIRATORY MASK

CROSS-REFERENCE TO RELATED APPLICATION

This application is a continuation of U.S. patent application Ser. No. 12/735,977, filed Aug. 27, 2010, which was the U.S. national phase of International Application No. PCT/AU2009/000240, filed Feb. 27, 2009, which designated the U.S. and claims the benefit of Australian Provisional Application No. AU 2008901057, filed Mar. 4, 2008, each of which is hereby incorporated herein by reference in its entirety.

FIELD OF THE INVENTION

The present invention relates to a respiratory mask used for treatment, e.g., of Sleep Disordered Breathing (SDB) with Continuous Positive Airway Pressure (CPAP) or Non-Invasive Positive Pressure Ventilation (NIPPY). In particular, the present invention relates to a respiratory mask with a foam contacting portion. Also, the present invention relates to a respiratory mask that is comfortable, easy to use and requires little maintenance.

BACKGROUND OF THE INVENTION

Typically, respiratory therapy is delivered in the form of a respiratory mask or mask system positioned between a patient and apparatus providing a supply of pressurized air or breathing gas. Mask systems in the field of the invention differ from mask systems used in other applications such as aviation and safety in particular because of their emphasis on comfort. This high level of comfort is desired because patients must sleep wearing the masks for hours, possibly every night for the rest of their lives. In addition, therapy compliance can be improved if the patient's bed partner is not adversely affected by the patient's therapy and wearing of the mask generally.

Mask systems typically have a highly clinical aesthetic (as will be described below). This may lead to patients becoming embarrassed about their therapy since the clinical aesthetic serves as a blatant reminder that they are ill and consequently can leave a negative perception of the patient in the mind of an observer.

Mask systems typically, although not always, comprise (i) a rigid or semi-rigid portion often referred to as a shell or frame, (ii) a soft, patient contacting portion often referred to as a cushion, and (iii) some form of headgear to hold the frame and cushion in position. If the mask system does include multiple components, at least some assembly and adjustment may be required, which can be difficult for patients who may suffer from lack of dexterity, etc. Further, mask systems often include a mechanism for connecting an air delivery conduit. The air delivery conduit may preferably be connected to a blower or flow generator.

Patient contacting portions, e.g., cushions, are typically constructed of a silicone material, but patient contacting portions including foam are known. For example, U.S. Pat. No. 5,429,683 (Le Mitouard) discloses a lining for a mask made of a polyurethane foam covered with skin (e.g., latex or silicone). However, skinned foam does not allow the portion in contact with the face to breathe, which can lead to skin irritation, and the sealing portion may be subject to creasing which may cause discomfort and lead to leak. The skin can also feel too hard for some patients, depending on the thickness and support structure. The skin also does not allow a high degree of local deformation and may be subject to tension transfer across its surface, which can result in shifting of the mask on the face and loss of seal/comfort.

A range of mask systems are known including nasal masks, nose & mouth masks, full face masks and nasal prongs, pillows, nozzles & cannulae. Masks typically cover more of the face than nasal prongs, pillows, nozzles and cannulae.

There is a continuous need in the art to provide mask systems with a high level of comfort and usability and a newly perceived need to provide mask systems having improved aesthetics.

SUMMARY OF THE INVENTION

One aspect of the invention is to provide an attachable interfacing portion for a respiratory mask.

Another aspect of the invention is to provide a removably attachable interfacing portion for a respiratory mask.

In an embodiment, the respiratory mask is a nasal mask, and the interfacing portion is a foam contacting portion that is arranged in use between the nose of the patient and the mask system. The foam contacting portion provides a seal between the nares of the patient and the mask system so as to deliver pressurized gas to the patient. The mask system may include a cushion, gusset and/or frame.

In one form, the nasal mask system may be provided with a releasable and replaceable foam contacting portion that it connected to the mask system by at least one connector.

In embodiments, the foam contacting portion may be connected to the mask system (e.g., connected to the frame, decoupling element, and/or headgear) by male and female connectors, a hook and loop arrangement, a press stud arrangement, hook and loop material, a clip arrangement, and/or an adhesive. In another embodiment, the foam contacting portion may be connected or otherwise provided to the mask system using existing structure on the frame, decoupling element, and/or headgear, e.g., without connectors and/or adhesive.

In another form, the nasal mask system may be provided with a removable foam contacting potion that adjoins to the mask system by wrapping about or around the mask system.

In one form, the foam contacting portion may be retrofitted to an existing nasal mask.

In another form, the foam contacting portion includes a foam sleeve that that may be slidingly positioned over a support structure. The foam sleeve may be removably positionable. In one form, the foam sleeve is sock-like.

Another aspect of the invention relates to a patient interface for delivering breathable gas to a patient including a foam interfacing portion adapted to provide a nasal interface to contact under and around the patient's nose in use and including an orifice adapted to surround both the patient's nares in use, and a positioning and stabilizing structure to support the foam interfacing portion in an operative position on the patient's face. The positioning and stabilizing structure is structured to provide a range of rotational, axial, and/or lateral movement to the foam interfacing portion while maintaining a sufficient interface and resisting the application of tube drag and/or headgear tension to the foam interfacing portion.

Other aspects, features, and advantages of this invention will become apparent from the following detailed description when taken in conjunction with the accompanying drawings, which are a part of this disclosure and which illustrate, by way of example, principles of this invention.

BRIEF DESCRIPTION OF THE DRAWINGS

The accompanying drawings facilitate an understanding of the various embodiments of this invention. In such drawings:

FIG. 9 depicts a rear view of the nasal mask of FIGS. 4 and 5;

FIG. 10 depicts a side view of a foam contacting portion according to an embodiment of the present invention;

FIG. 11 depicts a side view of an unassembled foam contacting portion and mask system according to an embodiment of the present invention;

DETAILED DESCRIPTION OF ILLUSTRATED EMBODIMENTS

The following description is provided in relation to several embodiments which may share common characteristics and features. It is to be understood that one or more features of any one embodiment may be combinable with one or more features of the other embodiments. In addition, any single feature or combination of features in any of the embodiments may constitute additional embodiments.

In this specification, the word "comprising" is to be understood in its "open" sense, that is, in the sense of "including", and thus not limited to its "closed" sense, that is the sense of "consisting only of". A corresponding meaning is to be attributed to the corresponding words "comprise", "comprised" and "comprises" where they appear.

The term "air" will be taken to include breathable gases, for example air with supplemental oxygen. It is also acknowledged that the positive airway pressure (PAP) devices or flow generators described herein may be designed to pump fluids other than air.

In broad terms, a patient interface in accordance with an embodiment of the invention may comprise three functional aspects: (i) interfacing, (ii) positioning and stabilizing, and (iii) air delivery. These three functional aspects may be constructed from one or more structural components, with a given structural component potentially fulfilling more than one function. For example, a mask frame may serve as part of a positioning and stabilizing function and allow the supply of air.

Figure 1:
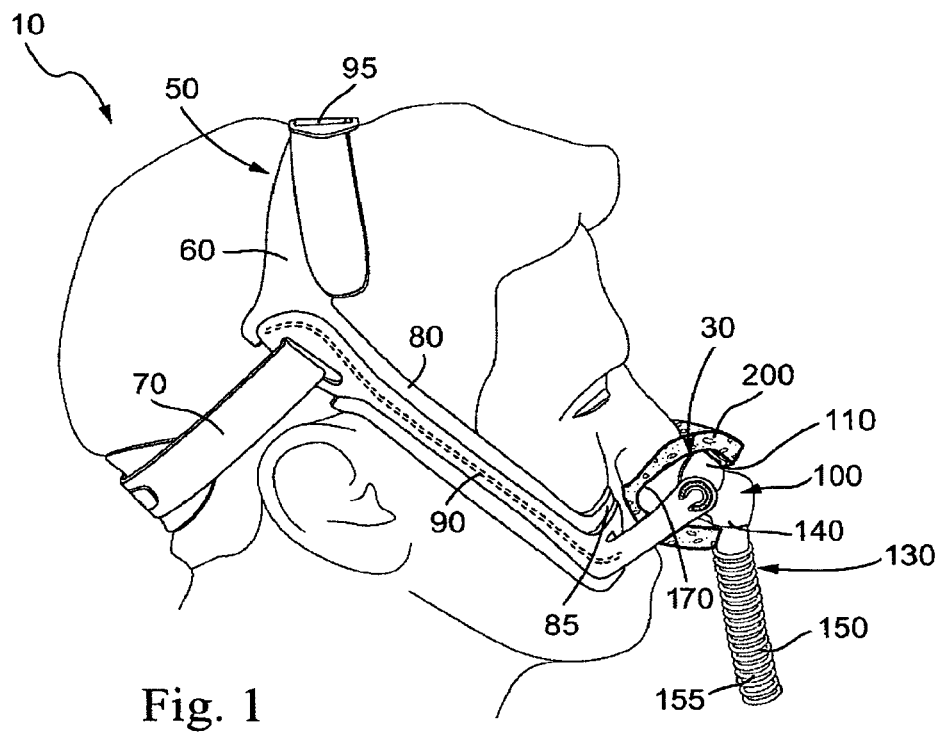
FIG. 1 depicts a side view of a nasal mask with a foam contacting portion in use according to an embodiment of the present invention.
Figure 2:
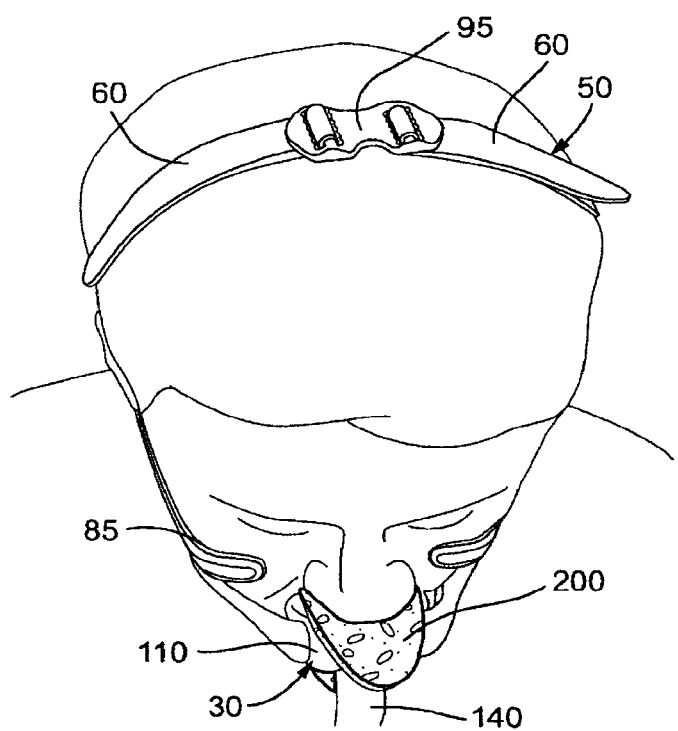
FIG. 2 depicts a top view of the nasal mask of FIG. 1.
Figure 3:
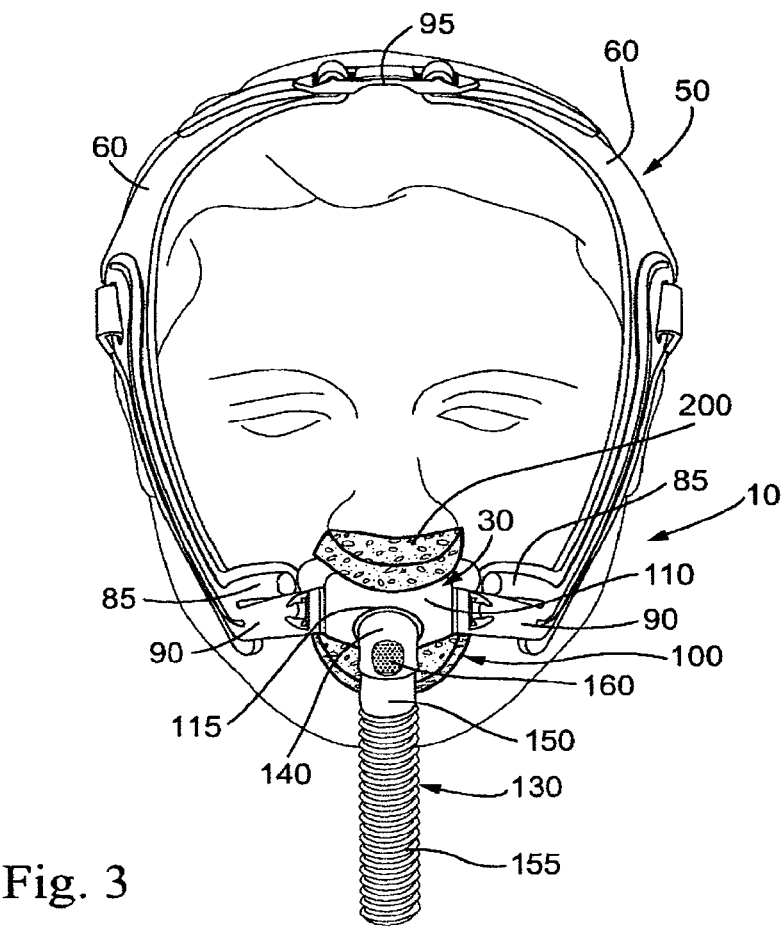
FIG. 3 depicts a front view of the nasal mask of FIG. 1.
Figure 4:
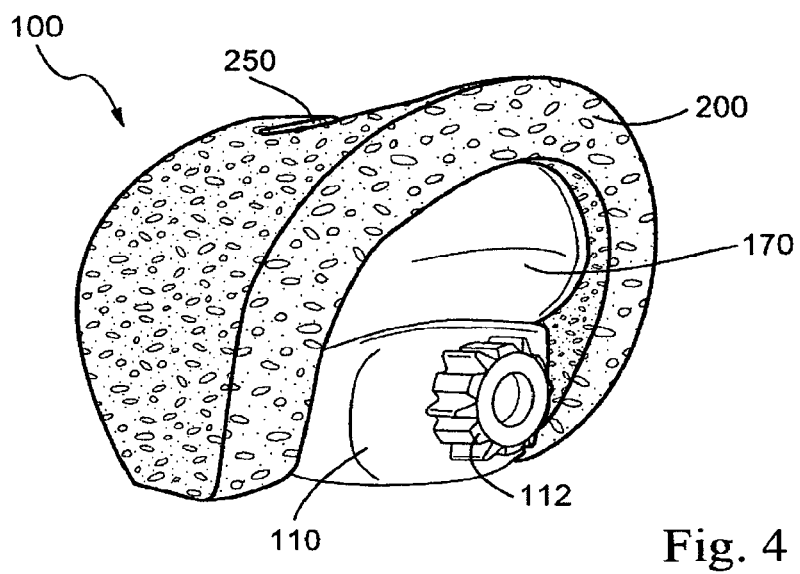
FIGS. 4 and 5 depict isometric views of a nasal mask with a foam contacting portion assembled according to an embodiment of the present invention.
Figure 5:
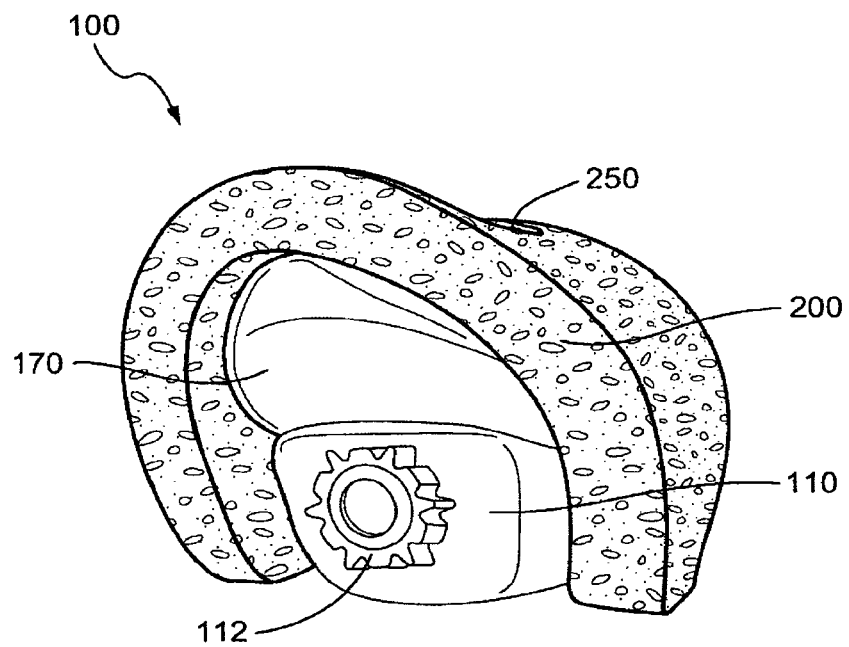
Figure 6:
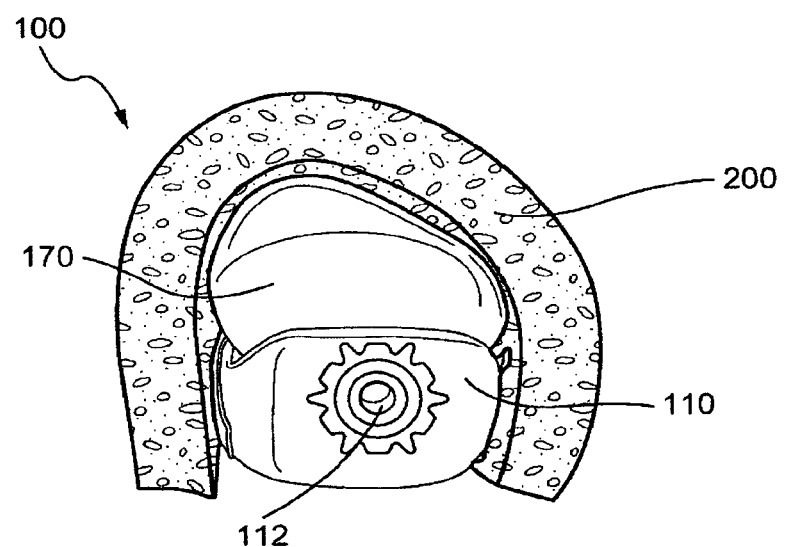
FIG. 6 depicts a side view of the nasal mask of FIGS. 4 and 5.
Figure 7:
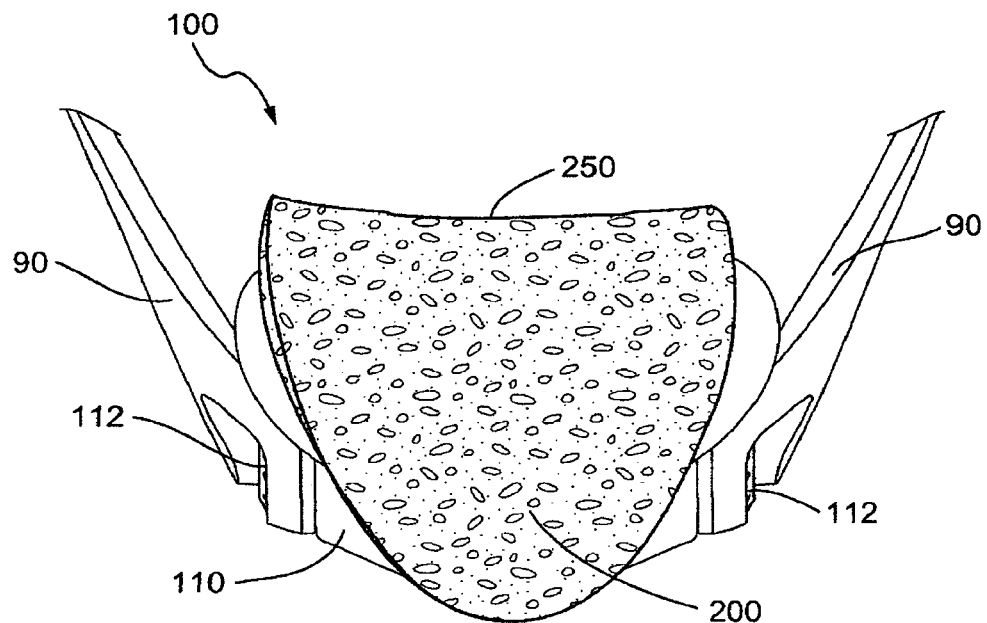
FIG. 7 depicts a front view of the nasal mask of FIGS. 4 and 5.
Figure 8:
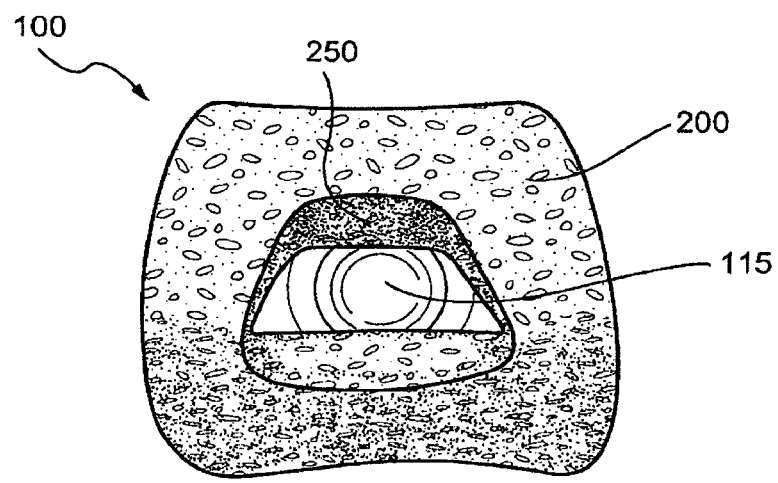
FIG. 8 depicts a top view of the nasal mask of FIGS. 4 and 5.

In an embodiment, as shown in FIGS. 1-3, the patient interface 10 may include a mask system 100, a positioning and stabilizing structure 30, and an air delivery system 130. Mask system 100 may include an interfacing portion 200. Positioning and stabilizing structure 30 may include a frame 110 and/or decoupling element 170 and/or a headgear 50 (that may include top straps 60, a back strap 70, one or more side straps 80 and rigidizers 90). Air delivery system 130 may include: an elbow 140 and a tube 150.

In addition, a patient interface 10 in accordance with an embodiment of the invention may perform other functions including venting of exhaled gases, decoupling of potentially seal disruptive forces and adjustment for different sized faces. Venting may be performed by different structures, e.g., such as the frame 110, the elbow 140 and/or the tube 150.

1. Interfacing
1.1 Introduction

In an embodiment, the interfacing function is provided by a nasal cushion (or "nasal cradle") that is placed at an entrance to the patient's nares. The nasal cushion is structured to form an interface with the nares and is shaped, oriented, sized and constructed so as provide a fit with a range of differently shaped and located flares.

The nasal cushion may be formed of foam (also referred to as a foam contacting portion). As shown generally in FIGS. 1-3, nasal cushion or foam contacting portion 200 may be positioned at the nares or under the nose. Foam contacting portion 200 may cushion the nares of the patient to increase comfort. Foam contacting portion 200 may also seal with the nares of the patient, e.g., if the foam is a closed cell foam. Alternatively, foam contacting portion 200 may be constructed from an open cell foam or a foam with some open cells, such that it allows a certain degree of leak while delivering sufficient pressure to the patient in the intended therapeutic effect. Instead, such a foam will allow some air to pass through the foam and leak gases into the atmosphere. This may be desirable to assist in venting.

In an embodiment, the foam contacting portion 200 may be maintained in position using stabilizing portions or rigidizers 90 attached to, or formed as part of headgear 50. In this form, the mask system 100 may be generally arranged per ResMed's MIRAGE SWIFT™ nasal pillows and as described in PCT Publication No. WO 2004/073778 (Gunaratnam et al), the contents of which are hereby expressly incorporated by cross-reference.

1.2 Foam

The foam used for the foam contacting portion 200 may be the same as that disclosed in PCT Publication No. WO 2008/070929 (Veliss et al), filed Dec. 14, 2007, which is incorporated herein by reference in its entirety. Alternatively, any suitable foam may be used, for example skinned foam.

In another embodiment, the cushion or foam contacting portion 200 of the mask system 100 may be the cushion disclosed in U.S. patent application Ser. No. 12/219,852 (Guney et al), filed Jan. 11, 2008, which is incorporated herein by reference in its entirety.

The foam contacting portion 200 may be a single piece of foam. In another form, the foam contacting portion 200 may be multiple pieces of foam joined together by any suitable means, for example gluing or insert molding.

Figure 12:
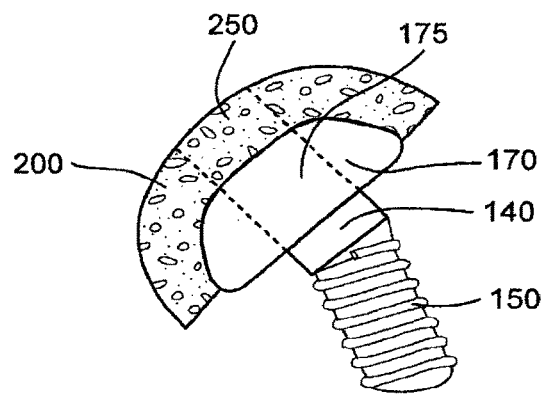
FIG. 12 depicts a side view of an assembled foam contacting portion and mask system according to an embodiment of the present invention.
Figure 13:
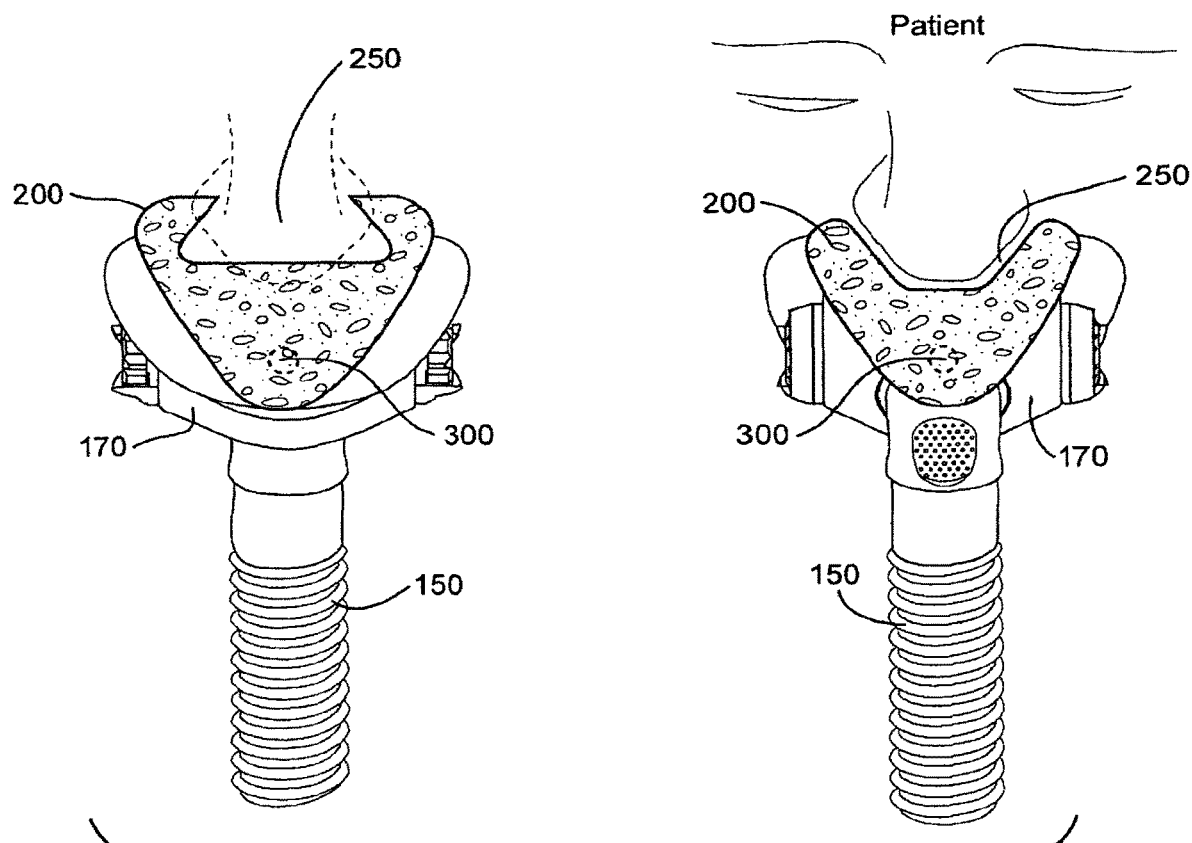
FIG. 13 depicts front and rear views of an assembled foam contacting portion and mask system in use according to an embodiment of the present invention.

As shown in the embodiment of FIGS. 4-9, the foam contacting portion 200 may have an orifice 250 for delivery of pressurized air. In one form, the orifice 250 provided to the foam contacting portion 200 will align with an orifice or aperture 175 or orifices in the decoupling element 170 (e.g., see FIGS. 11 and 12) and/or aperture 115 on frame 110 (e.g., see FIGS. 8 and 9) which is connected to elbow 140 and tube 150, so as to deliver pressurized gas to the patient. The orifice 250 or orifices provided to the foam contacting portion 200 may be the same size, smaller or larger than the aperture 175 and/or aperture 115.

In an embodiment, the thickness of foam contacting portion 200 may be 0.5-50 mm. For example, the thickness of foam contacting portion 200 may be 7-15 mm. In an exemplary embodiment, the thickness of foam contacting portion 200 may be 11 mm.

In an embodiment, the length of foam contacting portion 200 may be 10 mm-200 mm (or its largest length if it is not square). For example, the length of foam contacting portion 200 may be 40-120 min. In an exemplary embodiment, the length of foam contacting portion 200 may be 105 mm. In an embodiment, the width of foam contacting portion 200 may be 10 mm-100 mm (or its largest width if it is not square). For example, the width of foam contacting portion 200 may be 30-70 mm. In an exemplary embodiment, the width of foam contacting portion 200 may be 50 mm.

As disclosed in PCT Publication No. WO 2008/070929 (Veliss et al), the foam contacting portion may be impermeable or air permeable. Air permeability may give the foam interface a unique breathability, which acts to increase the comfort at the interface with the user's nose and skin. All air permeability aspects of PCT Publication No. WO 2008/070929 (Veliss et al) are incorporated herein by reference, and all embodiments in this disclosure may contain foam that is air permeable.

In another embodiment, the foam contacting portion 200 may be retrofitted to existing mask designs, for example ResMed's MIRAGE SWIFT™ as disclosed in U.S. Pat. No.

7,318,437 (Gunaratnam et al) and U.S. Patent Publication No. 2005/0241644 (Lynch et al), each of which is incorporated herein by reference.

1.3 Interface Attachment

Desirable features of an attachment mechanism of the foam contacting portion 200 to the positioning and stabilizing structure may include: satisfactory comfort, effective position of the interfacing portion and/or being easy to use. Due to the softness of foam, hard connecting pieces may in some forms be felt by the patient's face through the foam. Thus, attachment mechanisms that avoid such patient contact may be desired.

In another embodiment, the foam contacting portion 200 may be connected to a positioning and stabilizing structure such as a frame 110 and/or a decoupling element 170 or any other part of the mask system 100 by connecting elements such as hook and loop connectors, press studs, etc. Exemplary connecting elements are described below.

1.3.1 Wrap

In an embodiment, as shown in FIG. 4-13, the foam contacting portion 200 may be connected to a mask system 100 by wrapping the foam over or around the mask system 100. The foam contacting portion 200 may be secured in its wrapped position on the mask system 100 by a male connector 300 and female connector 310 or series of connectors 300, for example see FIGS. 9, 10-11, 13, 16 and 17. In the illustrated embodiment, the male connector 300 is provided to the foam contacting portion 200 and the female connector 310 is provided to the frame 110 and/or decoupling element 170. However, it should be appreciated that the reverse arrangement is possible, i.e., male connector may be provided to the frame and/or decoupling element and the female connector may be provided to the foam contacting portion.

Figures 15A, 15B, 15C, 15D:
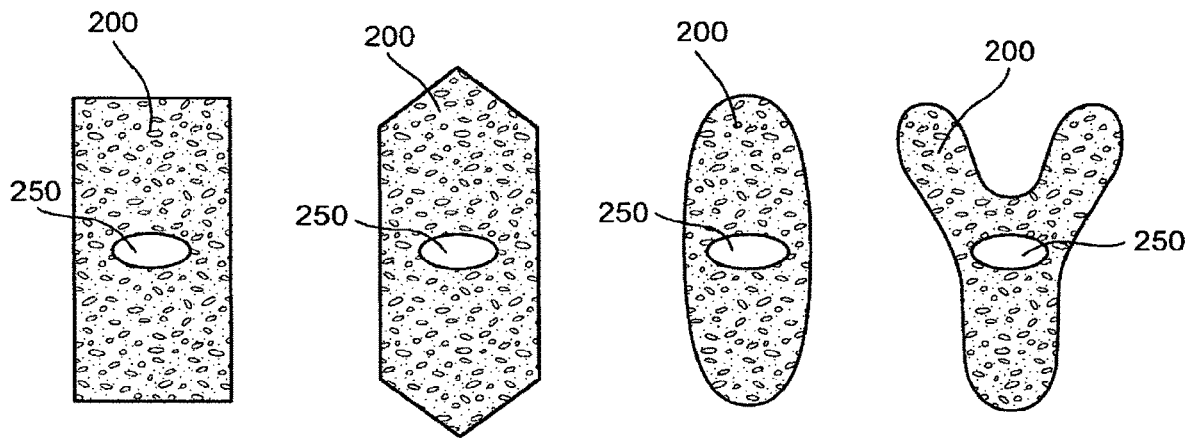
FIGS. 15A, 15B, 15C, and 15D depict top views of foam contacting portions according to embodiments of the present invention.
Figure 16:
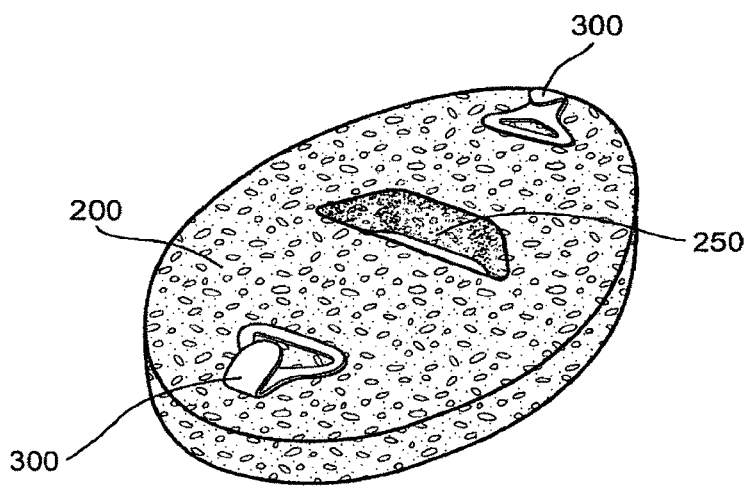
FIG. 16 depicts an isometric view of a foam contacting portion according to an embodiment of the present invention.
Figure 17:
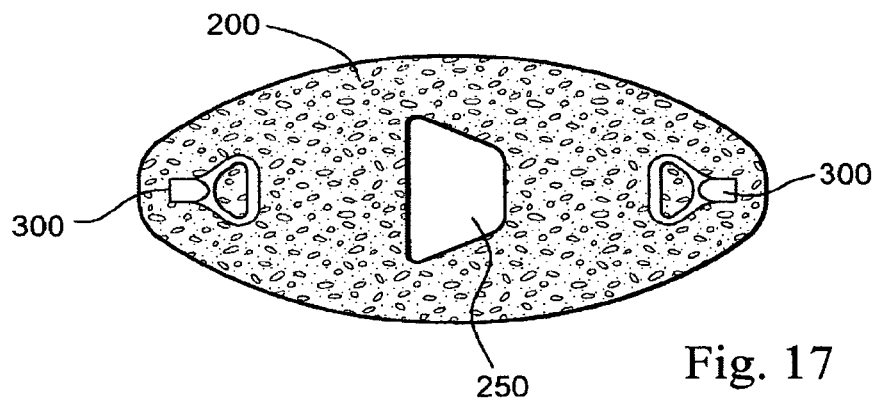
FIG. 17 depicts a rear view of the foam contacting portion of FIG. 16.
Figure 18:
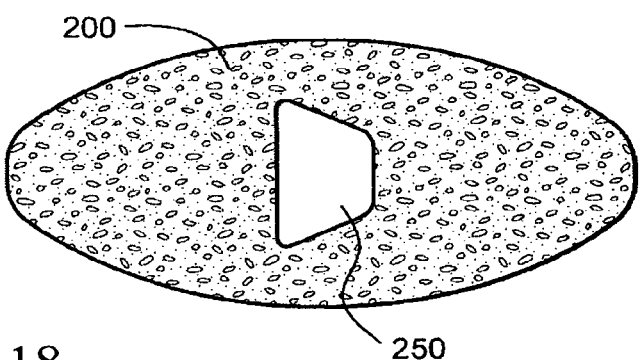
FIG. 18 depicts a top view of the foam contacting portion of FIG. 16.

The foam contacting portion 200 may be any shape such as generally rectangular (see FIG. 15A), oval (see FIGS. 15C and 16-18) or hexagonal (see FIG. 15B). Additionally, the foam contacting portion 200 may be any irregular shape, e.g., Y-shaped (see FIG. 15D).

As shown in FIG. 11, the foam contacting portion 200 may have male connectors 300 that engage with opposing female connectors 310 on the mask system 100. The female connectors 310 on the mask system 100 may be on a flexible component (for example, decoupling element 170). Alternatively, the female connectors 310 on the mask system 100 may be on a less flexible component (for example, frame 110).

The male connectors 300 may be fixed to the foam contacting portion 200 by a range of techniques, for example glue. The female connectors 310 may be fixed to the mask system 100 by a range of techniques, for example glue. In another form, the female connectors 310 may be co-molded to the mask system 100. However, the male and female connectors may be permanently or removably attached in other suitable manners.

Figure 19:
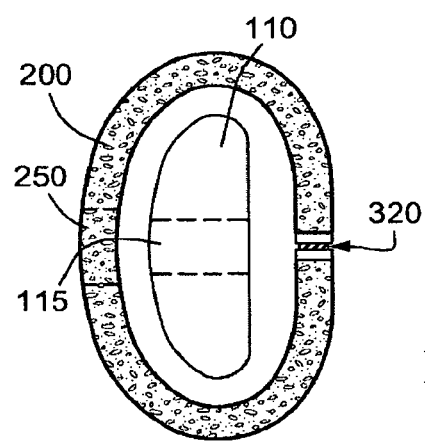
FIGS. 19, 20 and 21 depict various views of a foam contacting portion reconnecting to itself about a mask system according to an embodiment of the present invention.
Figure 20:
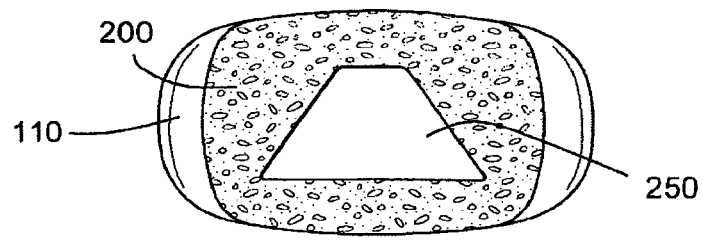
Figure 21:
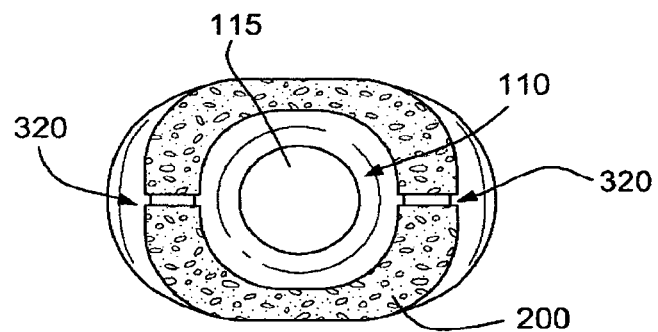
Figure 22:
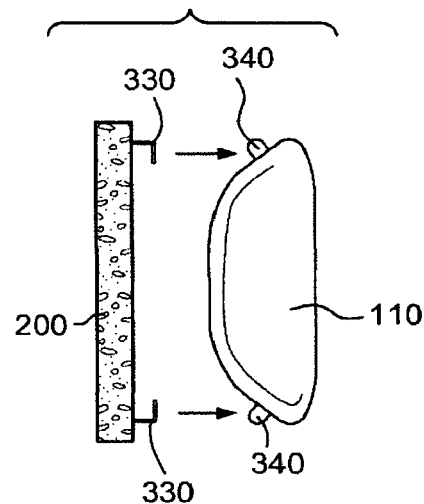
FIG. 22 depicts a side view of an unassembled foam contacting portion and mask system with a hook and loop connection according to an embodiment of the present invention.
Figure 23:
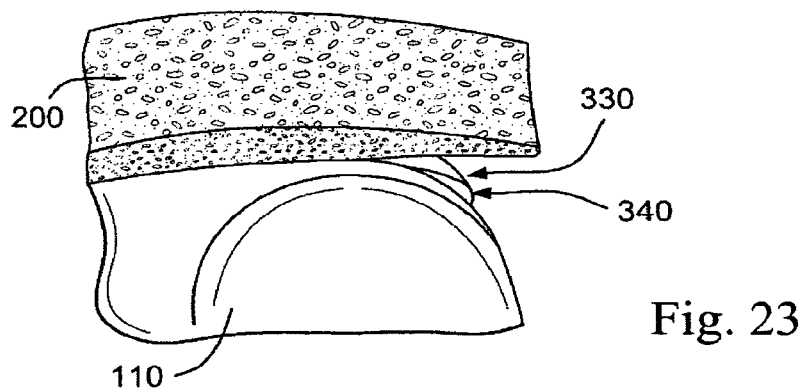
FIGS. 23 and 24 depict a side view of a hook and loop connection in assembly according to an embodiment of the present invention.
Figure 24:
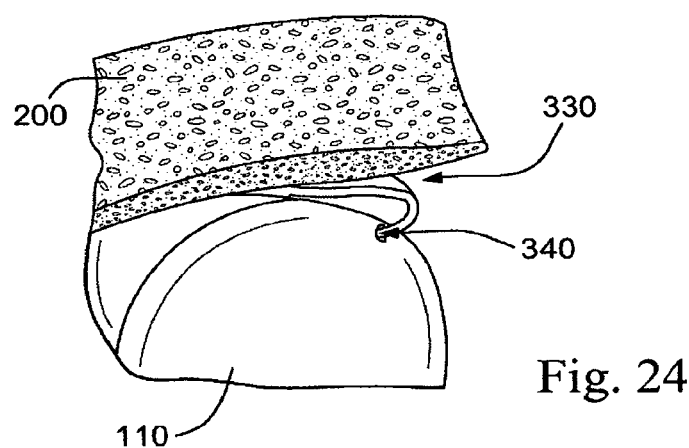
Figure 25:
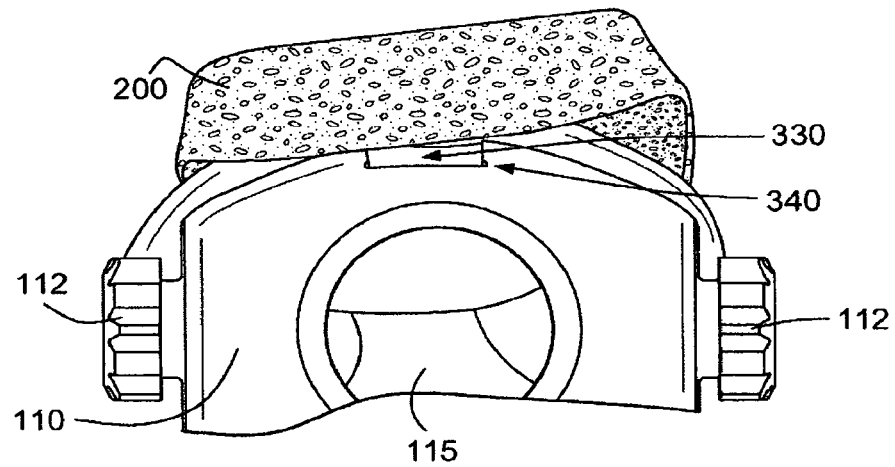
FIG. 25 depicts a rear view of a hook and loop connection in assembly according to an embodiment of the present invention.

In a further embodiment, the foam contacting portion 200 may not connect to the mask system 100 by male connectors 300 on the foam contacting portion 200 and female connectors 310 on the mask system 100, e.g., instead the foam contacting portion 200 may reconnect to itself. For example, as shown in FIG. 19-21, the male connectors 300 will be placed at one end of the foam contacting portion 200 with the female connectors 310 at the other end of the foam contacting portion 200, which can then be wrapped around the mask system 100 and connected together at connection points 320.

In another embodiment, the foam contacting portion may include a stretchable foam structured to expand or stretch to fit over the frame, decoupling element, etc., and then return to its original shape to tightly grasp the intended surface.

In a further embodiment, the connection mechanism may be via a hook 330 and loop 340 system, as shown in FIGS. 22-25. The male connectors 300 on the foam contacting portion 200 may take the form of hook 330. The female connectors 310 on the mask system 100 may take the form of loop 340. The loop 340 may be an additional piece attached to the mask system 100 or it may be a hole or aperture in the mask system 100 to allow engagement of the hook 330 (e.g., see FIGS. 23-25).

Figure 26:
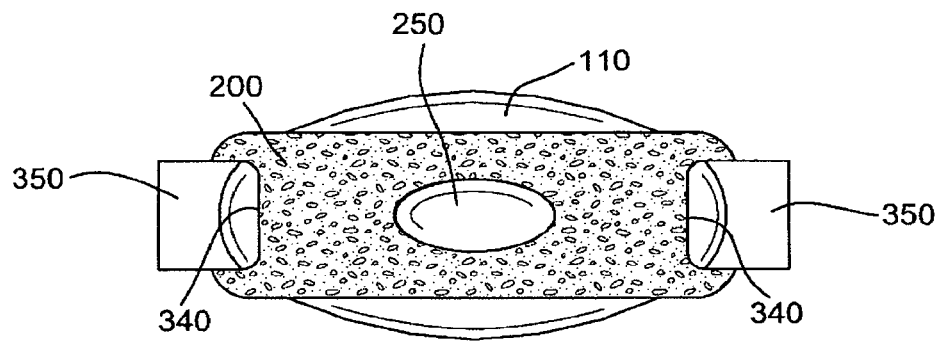
FIGS. 26, 27 and 28 depict various views of an assembled foam contacting portion and mask system with a hook and loop connection using headgear connectors according to an embodiment of the present invention.
Figure 27:
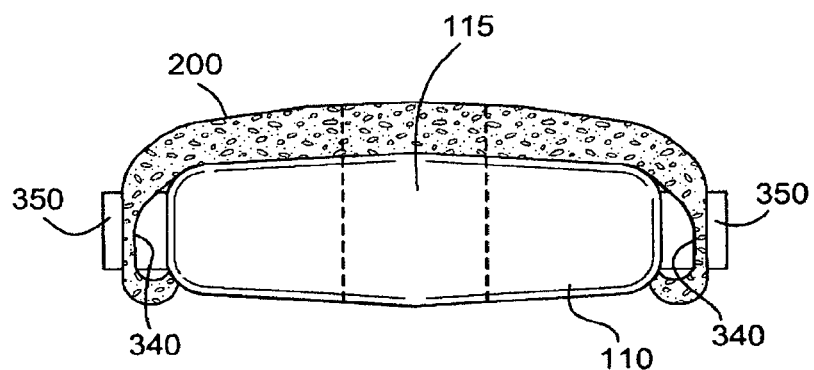
Figure 28:
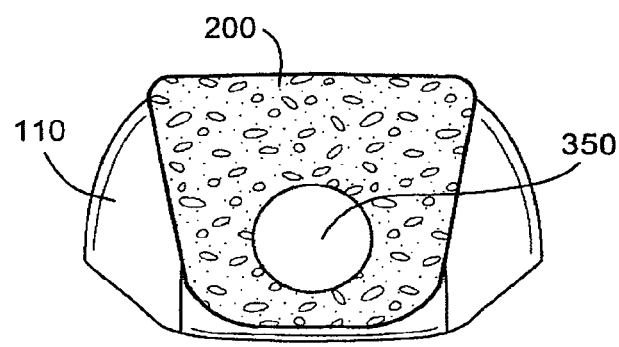
Figure 29:
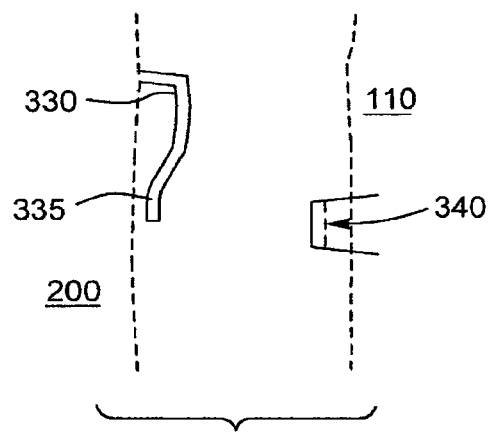
FIGS. 29 and 30 depict a side view of an unassembled foam contacting portion and mask system with a hook and loop connection using a detent according to an embodiment of the present invention.
Figure 30:
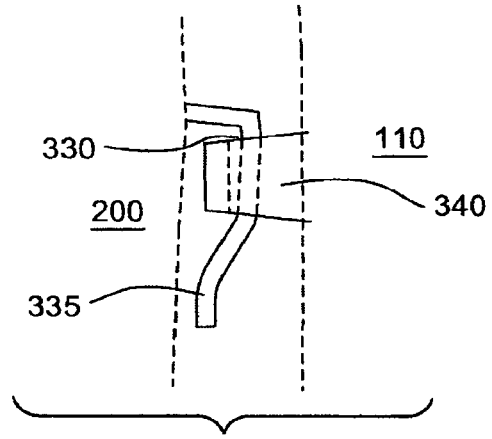

Alternatively, the reverse arrangement is possible (i.e., loop 340 or hole on the foam contacting portion 200 and hook 330 on the mask system 100). In this form, the loop 340 may be a hole in the foam contacting portion 200, and the hook 330 on the mask system 100 may be an attached or co-molded hook 330 or may be a pre-existing structure on the mask system 100. For example, FIGS. 26-28 illustrate an embodiment in which connectors 350 on the frame 110 (e.g., headgear connecting portions for attaching headgear) extend through respective openings 340 provided to ends of the foam contacting portion. In yet another form, the hook 330 may have a detent 335 to ensure retention of the loop 340, as shown in FIGS. 29-30. The hook 330 and loop 340 may be made from a range of different materials or combination of materials, including but not limited to: wire, silicone, polycarbonate, polypropylene, TPE, polyethylene or any other suitable material.

Figure 31:
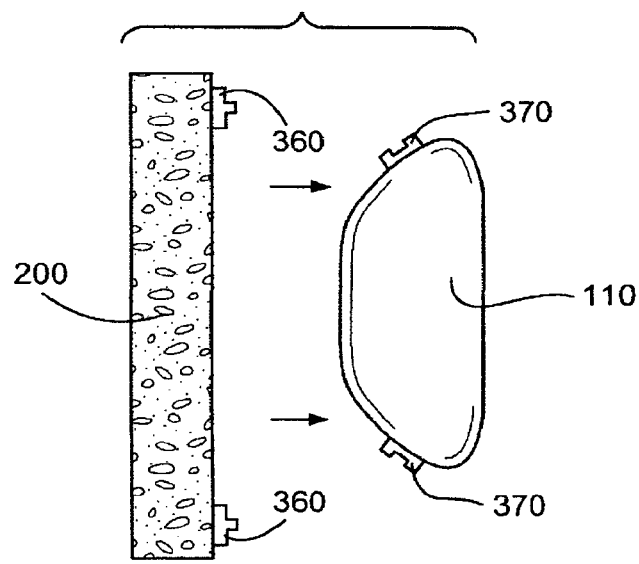
FIG. 31 depicts a side view of an unassembled foam contacting portion and mask system with a stud connection according to an embodiment of the present invention.
Figure 32:
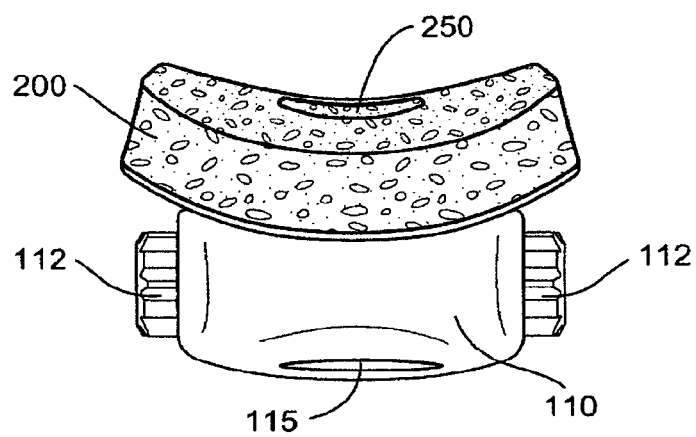
FIG. 32 depicts a front view of an assembled foam contacting portion and mask system with a clipped connection according to an embodiment of the present invention.
Figure 33:
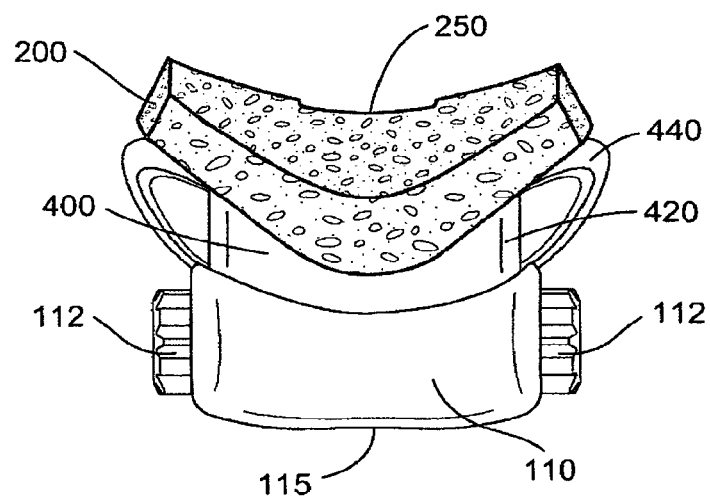
FIG. 33 depicts a back view of an assembled foam contacting portion and mask system with a clipped connection according to an embodiment of the present invention.
Figure 34:
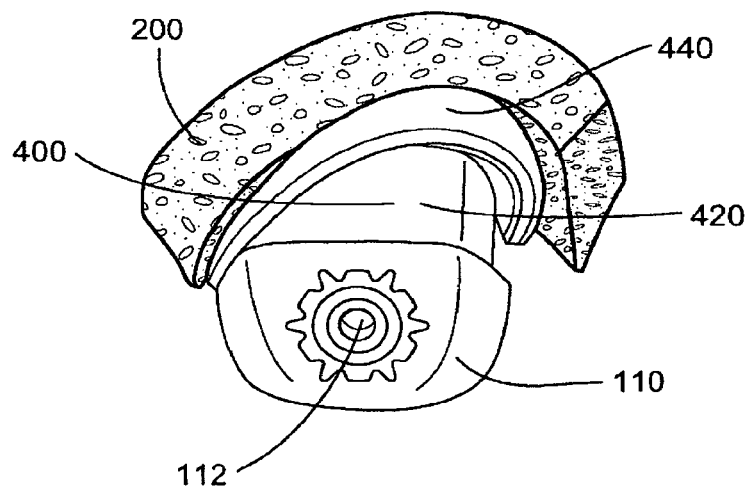
FIG. 34 depicts a side view of an assembled foam contacting portion and mask system with a clipped connection according to an embodiment of the present invention.
Figure 35:
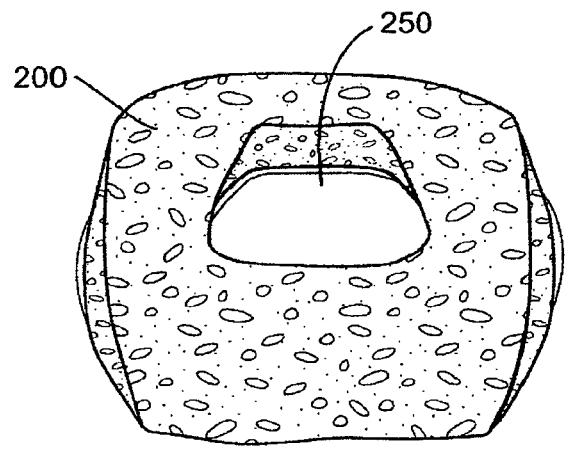
FIG. 35 depicts a top view of an assembled foam contacting portion and mask system with a clipped connection according to an embodiment of the present invention.
Figure 36:
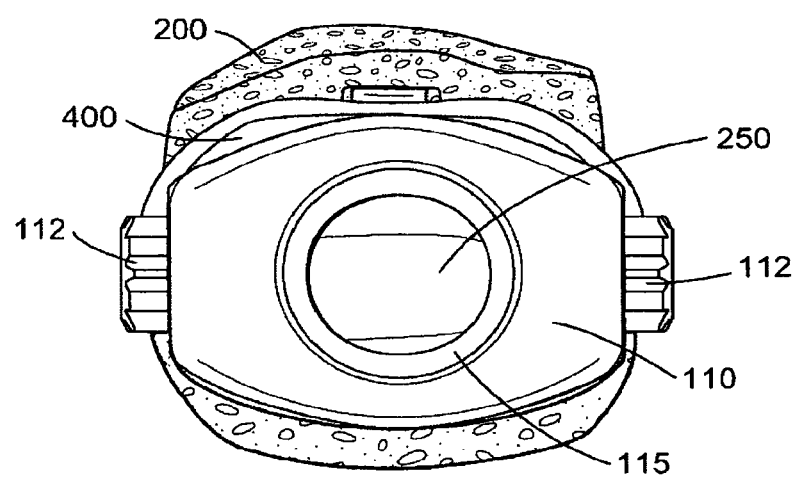
FIG. 36 depicts a rear view of an assembled foam contacting portion and mask system with a clipped connection according to an embodiment of the present invention.
Figure 37:
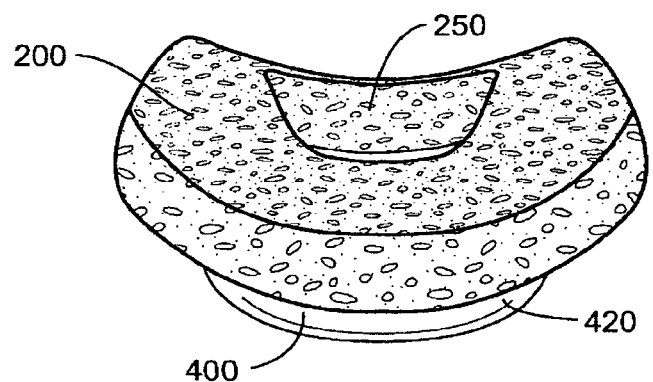
FIG. 37 depicts a front view of a foam contacting portion with a clip connection according to an embodiment of the present invention.
Figure 38:
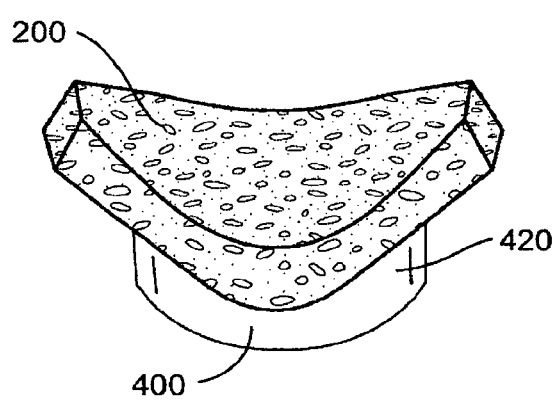
FIG. 38 depicts a back view of a foam contacting portion with a clip connection according to an embodiment of the present invention.
Figure 39:
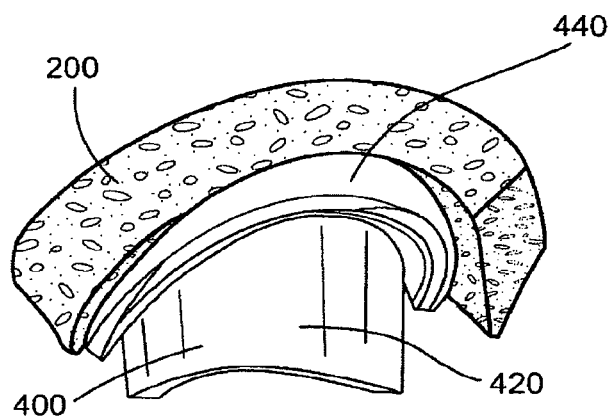
FIG. 39 depicts a side view of a foam contacting portion with a clip connection according to an embodiment of the present invention.
Figure 40:
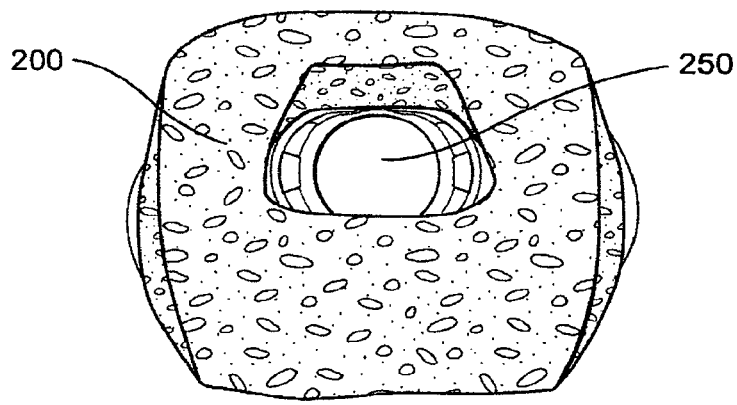
FIG. 40 depicts a top view of a foam contacting portion with a clip connection according to an embodiment of the present invention.
Figure 41:
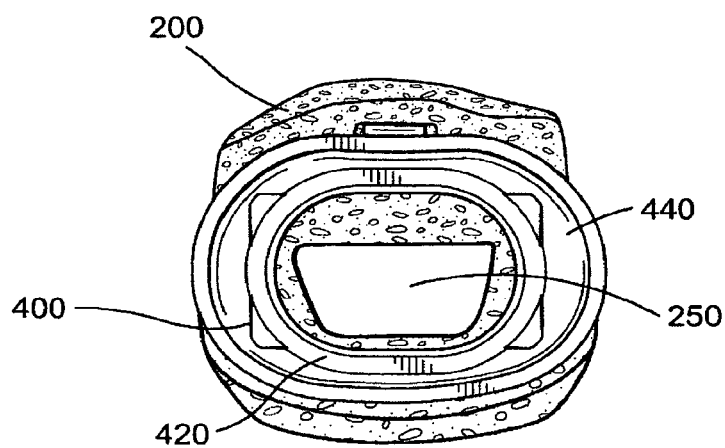
FIG. 41 depicts a rear view of a foam contacting portion with a clip connection according to an embodiment of the present invention.

In a further embodiment, the connection mechanism may be achieved by a press stud 360 as shown in FIG. 31. The male connectors 300 on the foam contacting portion 200 may take the form of a stud 360. The female connectors 310 on the mask system 100 (e.g., frame 110 or decoupling element 170) may take the form of a hole or recess 370. Alternatively, the reverse arrangement is possible (i.e., hole 370 on the foam contacting portion 200 and stud 360 on the mask system 100). The press stud 360 may be made from materials such as metals, polymers or any other suitable material.

In a further embodiment, as shown in FIGS. 44-47, the foam contacting portion 200 may be provided with apertures 380 that are intended to be positioned adjacent alignment holes 180 on the mask system 100. A pin or anchor 390 may be used to secure foam contacting portion 200 onto mask system 100 by inserting the anchor 390 through apertures 380 and alignment holes 180 (see FIG. 47). Anchor 390 may have one or more locking portions 395 so that once in position, the foam contacting portion 200 remains in its position on the mask system 100.

In a further embodiment, the foam contacting portion 200 may be wrapped onto or around the mask system 100 and connected by other type of mechanisms, including but not limited to hook and loop material (e.g., Velcro') or magnets.

In a further embodiment, the wrapped foam contacting portion 200 may be permanently connected to the mask system 100, for example, by gluing, welding or co-molding. For example, the mask system 100 may be made from a foam that can be co-molded with another foam to form the foam contacting portion 200. In yet another embodiment, the foam may be a flocking foam that is provided to (e.g., sprayed onto) the frame, decoupling element, etc.

Exemplary benefits of the wrapped foam contacting portion 200 may include: the ease of sealing the foam contacting portion with the patient and the mask system, continuity of feel, top lip comfort, retro-fitability, intuitiveness of assembly and mass production capability. Other benefits of the wrapped foam may include: if the intention is to replace the foam contacting portion on a regular basis (e.g., daily, weekly or monthly—as disclosed in PCT Publication WO 2008/070929 (Veliss et al)), the portion that is disposed of is small compared to the mask system. This embodiment therefore minimizes waste and maximizes efficiencies around the packaging, storage and transportation of the replacement foam contacting portions.

1.3.2 Clip

In another form, the foam contacting portion 200 may be connected to a mask system 100 by clipping the foam into the mask system 100. The foam contacting portion 200 may be secured in its clipped position on the mask system 100, e.g., by an interference fit.

Figure 48:
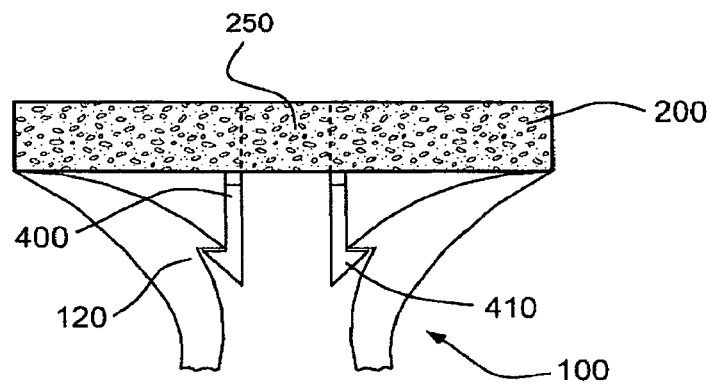
FIG. 48 depicts a side view of a mask system according to an embodiment of the present invention.
Figure 49:
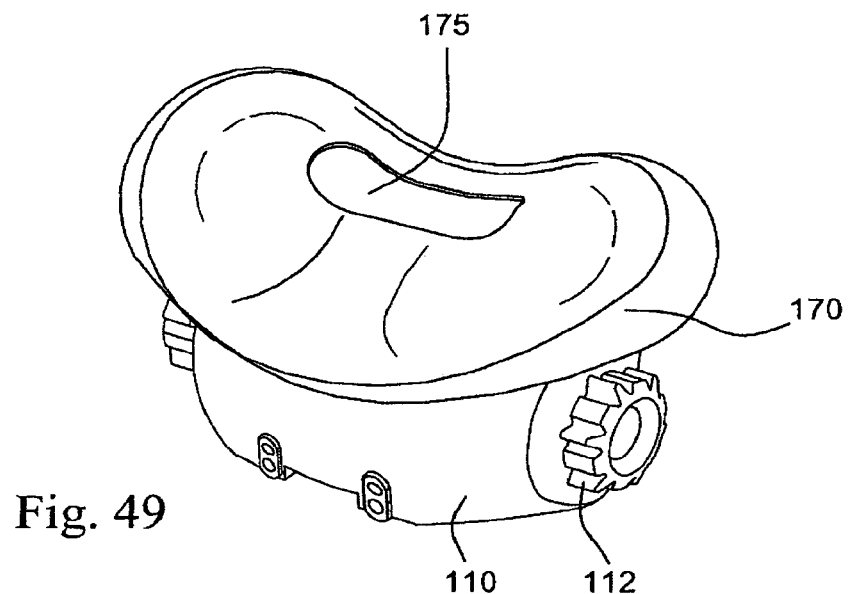
FIG. 49 depicts an isometric view of a support structure according to an embodiment of the present invention.
Figure 50:
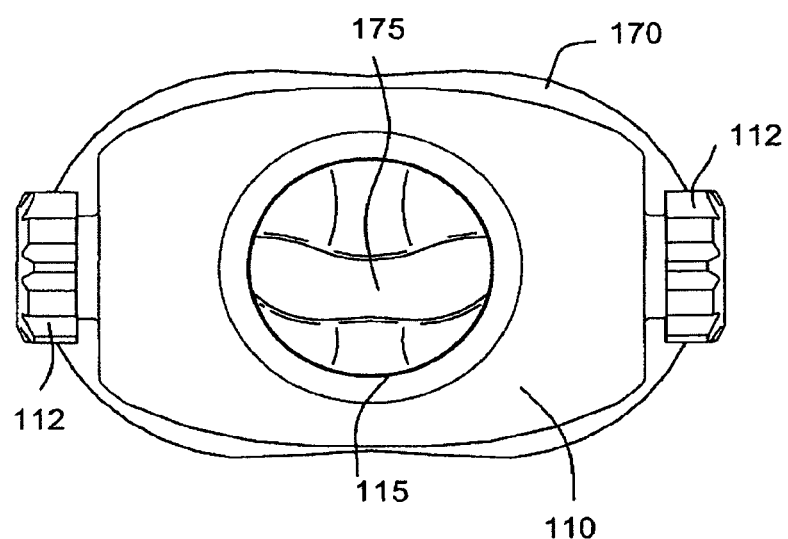
FIG. 50 depicts a bottom view of the support structure of FIG. 49.
Figure 51:
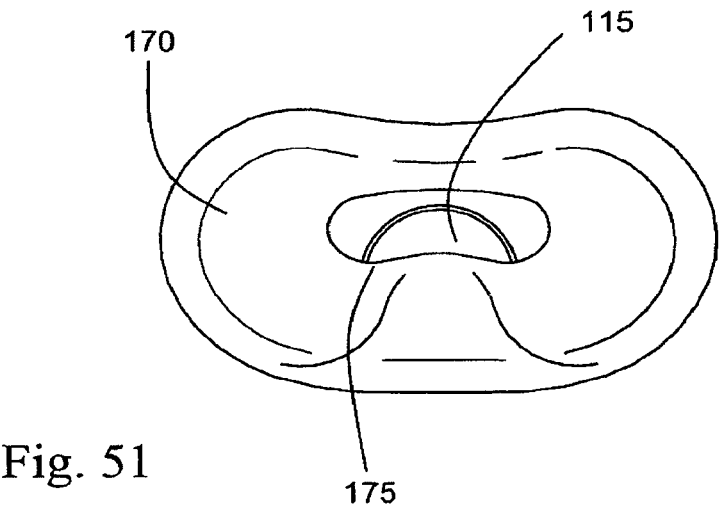
FIG. 51 depicts a top view of the support structure of FIG. 49.
Figure 52:
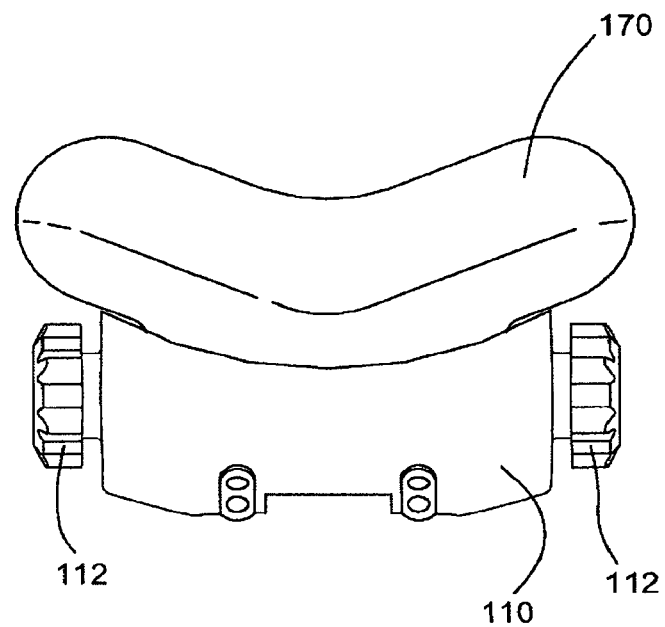
FIG. 52 depicts a front view of the support structure of FIG. 49.
Figure 53:
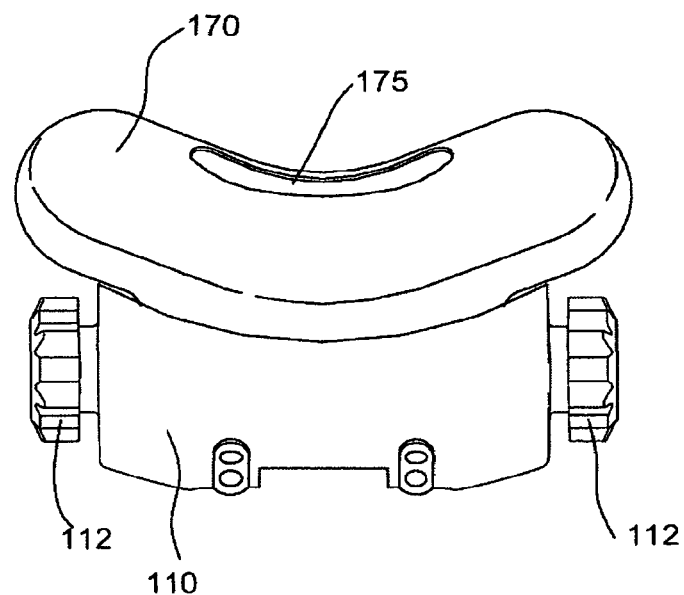
FIG. 53 depicts a rear view of the support structure of FIG. 49.
Figure 54:
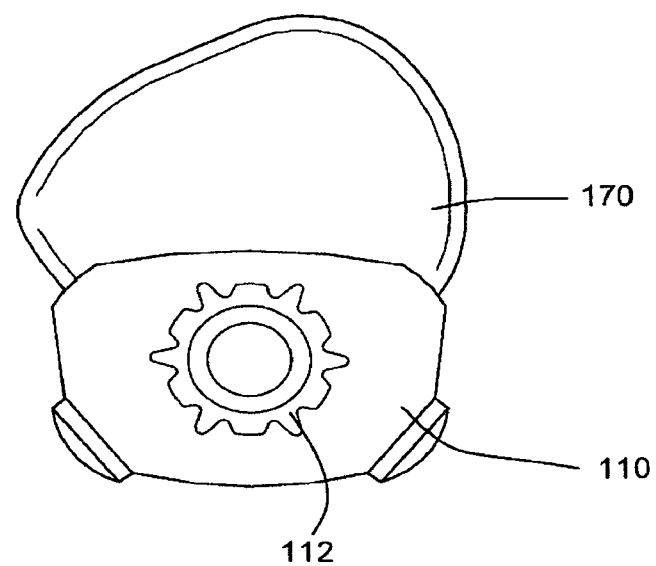
FIG. 54 depicts a side view of the support structure of FIG. 49.
Figure 55:
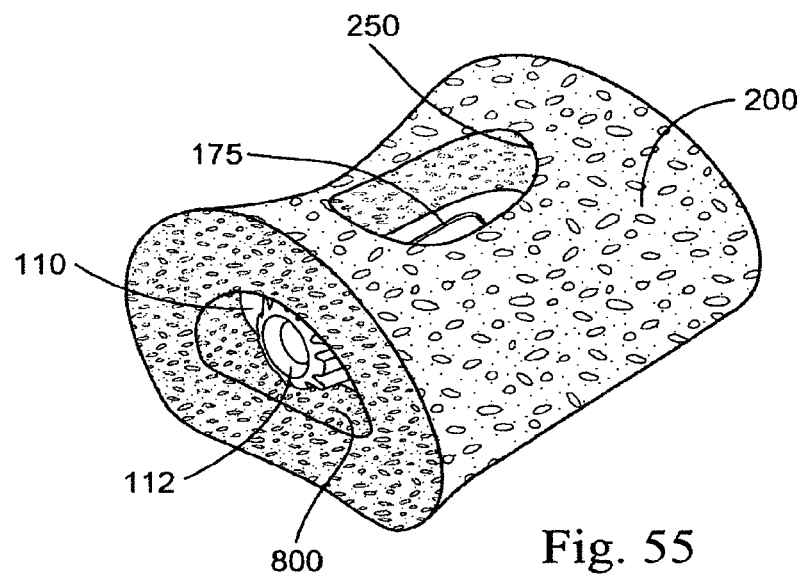
FIG. 55 depicts an isometric view of a mask system according to an embodiment of the present invention.
Figure 56:
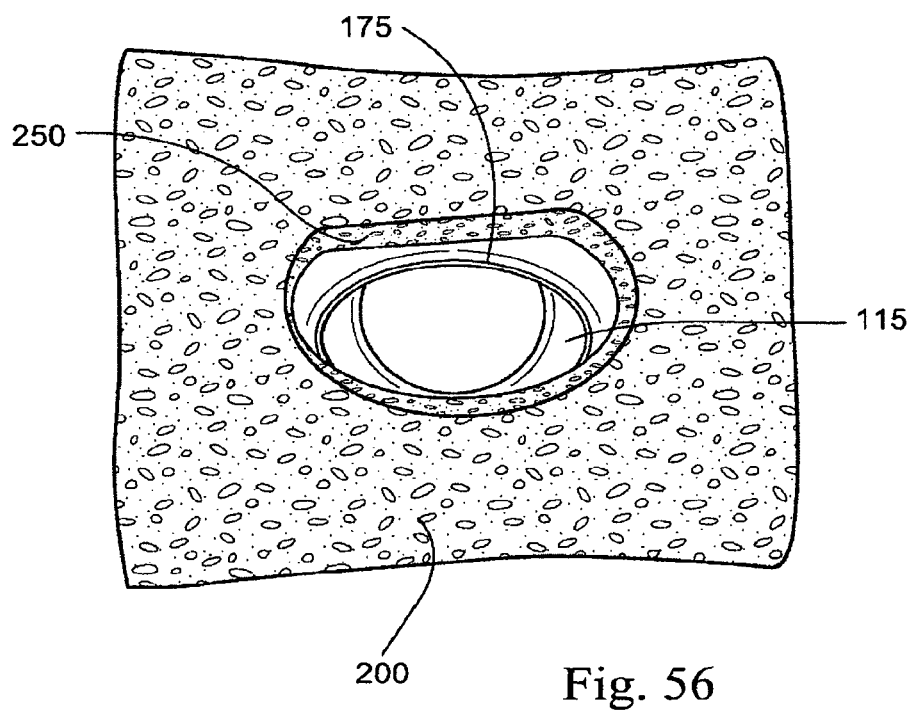
FIG. 56 depicts a top view of the mask system of FIG. 55.
Figure 57:
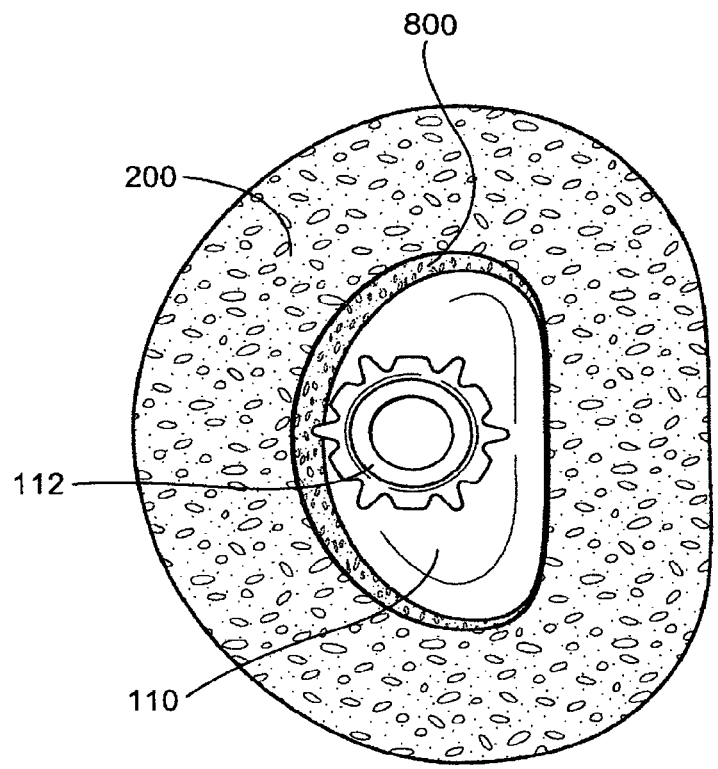
FIG. 57 depicts a side view of the mask system of FIG. 55.
Figure 58:
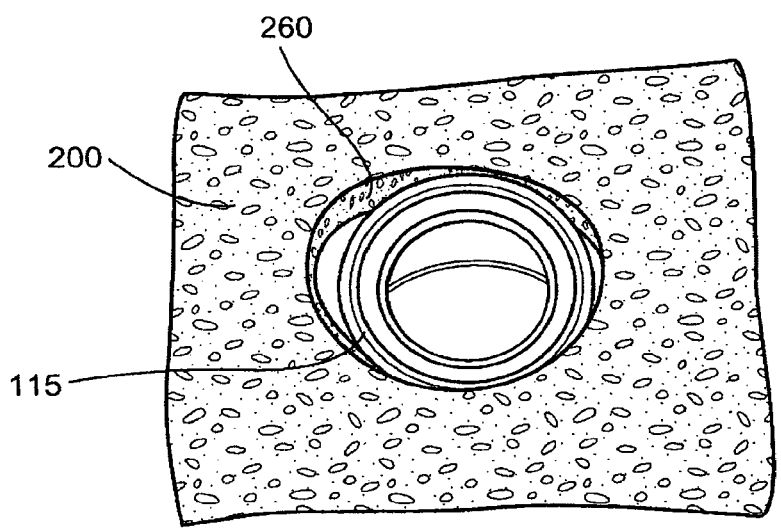
FIG. 58 depicts a bottom view of the mask system of FIG. 55.
Figure 59:
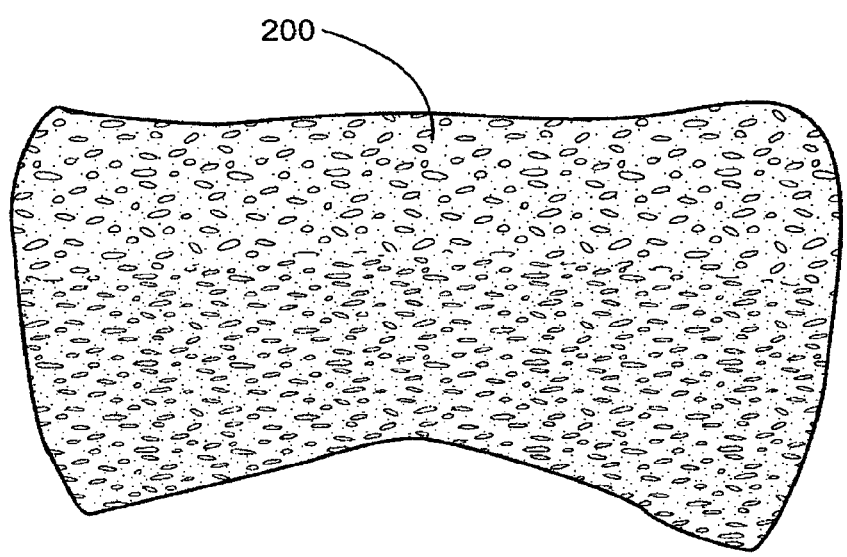
FIG. 59 depicts a front view of the mask system of FIG. 55.

FIGS. 32-36 show foam contacting portion 200 clipped into the mask system 100 by a clip 400. Clip 400 is slidably engaged with mask system 100 and secures by an interference fit with a portion (e.g., frame 110) of the mask system 100. In an embodiment, clip 400 may be interference fit via locking bumps 410 with step 120 on mask system 100 (see FIG. 48). In an alternative embodiment, clip 400 may be secured in place by another other means, including but not limited to: screw type mechanism. In another alternative embodiment, the clip 400 may be permanently secured to mask system 100, for example, by adhesive. In another alternative embodiment, clip 400 may be co-molded or be continuous with the mask system 100.

The clip 400 may be fixed to the foam contacting portion 200 permanently, for example by adhesive or co-molding. Alternatively, clip 400 may be releasably connected to foam contacting portion 200, including but not limited to: hook and loop material (e.g., Velcro™.

In an embodiment, clip 400 may have a support structure 420 that may have a generally elliptical cross section (e.g., see FIGS. 33, 34, 37-39, and 41). Support structure 420 may engage with mask system 100 to secure the foam contacting portion 200 in place. Support structure 420 may also assist in presenting the foam contacting structure 200 at a desirable orientation to the patient's nose. Support structure 420 may be hollow to allow the flow of pressurized gas from air delivery tube 150 to orifice 250 of foam contacting portion 200.

In an embodiment, clip 400 may comprise an upper surface 440 that engages with foam contacting portion 200 (e.g., see FIGS. 33, 34, 39, and 41). Upper surface 440 may be generally planar. In an exemplary embodiment, upper surface 440 may be curved to conform to the contours of the patient's face to improve comfort and seal of the mask. Upper surface 440 may be as wide as the foam contacting portion 200. Alternatively, upper surface 440 may be smaller or less wide than the foam contacting portion 200 such that the outer edge of foam contacting portion 200 is able to overhang the upper surface 440 and thus flex at its edge. This arrangement may allow the foam contacting portion to better conform to the patient's face.

1.3.3 Other

In a further embodiment, the foam contacting portion 200 need not be connected to the mask system 100 via connecting elements. Rather, the foam contacting portion 200 may be placed on the mask system 100 by other means such as pulled over (e.g., like a sock). For example, as shown in FIGS. 55-59, contacting portion 200 may be a cylindrical or continuous portion of foam with an opening 800 to receive the frame 110 and headgear connecting portions 112. Foam contacting portion 200 may also have orifice 250 for interfacing with aperture 175 in decoupling portion 170 to allow the delivery of breathable gas to the patient. Foam contacting portion 200 may also have opening 260 for interfacing with aperture 115 of frame 110.

Figure 14:
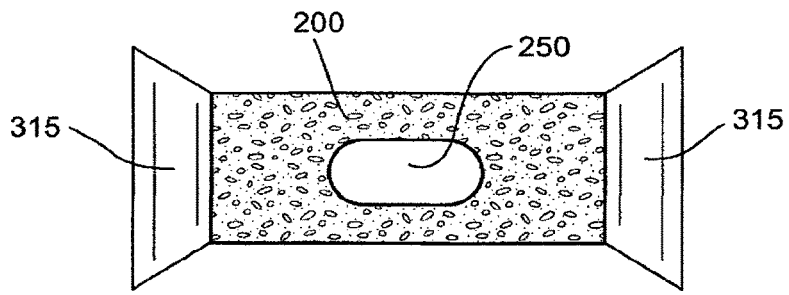
FIG. 14 depicts a top view of a foam contacting portion with an intermediate connecting structure according to an embodiment of the present invention.

In another embodiment, the foam contacting portion 200 may be connected to an intermediate connecting structure 315 (see FIG. 14). This intermediate connecting structure 315 may connect to the foam contacting portion 200 on one side and connect to the mask system 100 on the other side. This may include but is not limited to: the foam contacting portion 200 may be connected to a piece of flexible fabric material (e.g., Breath-O-Prene™ by Accumed) which is then connected to the mask system 100 (or part(s) of the mask system 100). Alternatively, the intermediate connecting structure 315 shown in FIG. 14 may not connect to the mask system 100, instead it may wrap around the mask system and the left and right intermediate connecting structures 315 may connect to each other.

In a further embodiment, the foam may be fixed (e.g., using an adhesive) to an adaptor or clipping mechanism, which in turn connects via an interference fit onto the mask frame.

1.4 Interface Size

In a further embodiment, the foam may be provided in various sizes to accommodate varying anthropometric requirements. Typical nasal pillow designs have sizes based on the nostrils of the population as these pillows seal around the nares. However, the same sizing may not be ideal for the foam contacting portion 200 as it does not seal on the edge of, or inside the nares. Instead sizing may be based on sealing against the area around the nares (as indicated by the dashed line d1 around the nares in FIG. 42).

Figure 42:
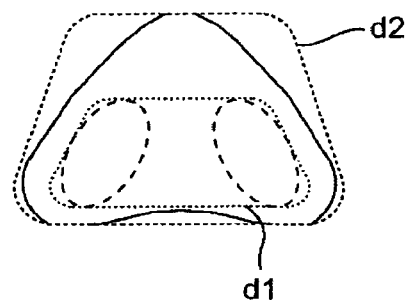
FIGS. 42 and 43 depict the naris region of a patient.

FIG. 42 presents a two-dimensional view of the underside of the nose and defines the areas that may be considered for sealing the nostrils. The orifice 250 on the foam contacting portion 200 should be within the bounds of the area of the nose (shown by the dashed line d2 in FIG. 42) so that the mask can sealingly engage with the nose. Should the orifice 250 be any larger than the region of the nose (dashed line d2), the mask may leak. In an embodiment, the orifice 250 should not be any smaller than the region within the nares (shown by the dashed line d1) so as to occlude the patient's airway. The orifice in the foam may encroach on the nostril openings on some noses and some degree of partial occlusion may be acceptable.

In a further embodiment, there may be one orifice 250 in the foam contacting portion 200. In one form, the orifice 250 in the foam contacting portion 200 may be generally trapezoidal or 'D' shaped as shown in FIGS. 8, and 16-18. In another form, the orifice 250 may be circular or oval (as shown in FIGS. 14 and 15A-15D), square (not shown) or any other shape fitting within the aforementioned limits.

Figure 43:
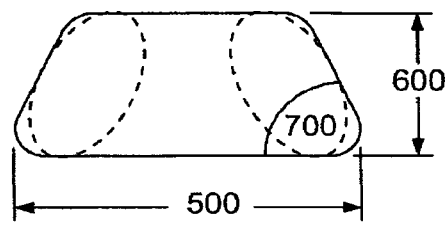
Figure 44:
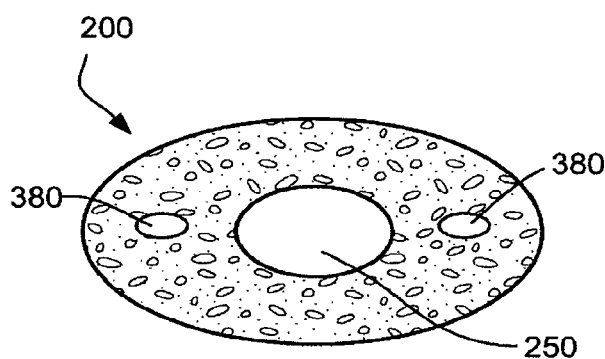
FIG. 44 depicts a top view of a foam contacting portion according to an embodiment of the present invention.
Figure 45:
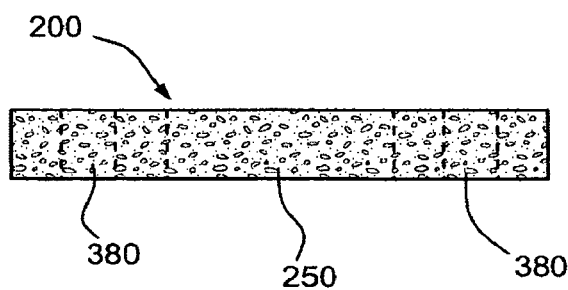
FIG. 45 depicts a side view of the foam contacting portion of FIG. 44.
Figure 46:
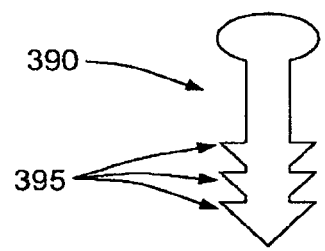
FIG. 46 depicts a side view of a locking pin according to an embodiment of the present invention.
Figure 47:
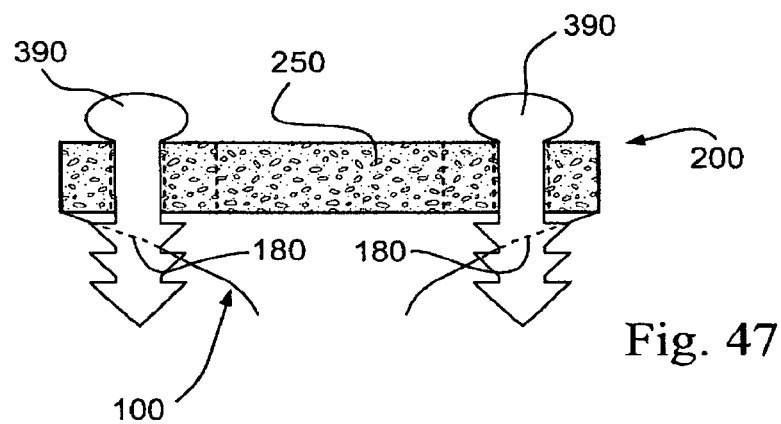
FIG. 47 depicts a side view of a mask system according to an embodiment of the present invention.

In a further embodiment and referring to FIG. 43, the orifice 250 in the foam contacting portion 200 may be 15-50 mm wide (indicated in FIG. 43 by dimension 500). In an exemplary embodiment, the orifice 250 in the foam contacting portion 200 may be about 22 mm wide. In another exemplary embodiment, the orifice 250 in the foam contacting portion 200 may be about 31 mm wide. In an embodiment, the orifice 250 in the foam contacting portion 200 may be 5-30 mm high (indicated in FIG. 43 by dimension 600). In an exemplary embodiment, the orifice 250 in the foam contacting portion 200 may be about 11 mm high. In another exemplary embodiment, the orifice 250 in the foam contacting portion 200 may be about 16 mm high.

In a further embodiment, the orifice 250 in the foam contacting portion 200 may have an angle of 10-80° (indicated in FIG. 43 by dimension 700). In an exemplary embodiment, angle 700 is about 67°. In another exemplary embodiment, angle 700 is about 50°.

In a further embodiment, there may be more than one orifice 250 in the foam contacting portion 200. In one form, there may be two orifices 250, e.g., each generally oval in shape. In another form, there may be a plurality of orifices 250 (for example, 3, 4, 5, 10 or more), e.g., each that are generally round. In another form, there may be multiple orifices 250 of any shape, within the limits shown above (indicated by the dashed lines d1 and d2 in FIG. 42).

2. Positioning and Stabilizing Structure 2.1 Introduction

A patient interface 10 provides a structure for suitable positioning, suspension and stabilizing of the interfacing portion 200 of the patient interface 10 at an entrance to the airways of the patient. This structure includes: the decoupling element 170, the frame 110 and headgear 50 with rigidizers 90. The decoupling element 170 acts as a form of suspension system or force insulation system whereby it isolates forces from one portion of the patient interface 10 from another portion of the patient interface 10. The headgear 50 and rigidizers 90 form a structure that may resist bending in one or more directions (and/or from tube drag) and yet is flexible to conform to different facial geometries, or to move in response to other potentially disruptive forces. In combination with the suspension system, a greater range of movement of a mask system in accordance with an embodiment of the invention can be accommodated without disrupting the seal than in prior art mask systems.

2.2 Frame

A frame 110 in accordance with an embodiment of the present invention as shown in FIGS. 49-54, serves a number of functions, including: a connection point to decoupling element 170, headgear rigidizers 90 and elbow 140. A given functional feature may reside in different structures. For example, the stabilizing portion of headgear 50 may be formed as part of a frame 110 either additionally or alternatively.

Frame 110 may connect to the elbow 140 via aperture 115, whereby the elbow clips into the aperture 115, or interfaces with the aperture 115 by any such means so as to join the elbow 140 to the frame 110. Frame 110 may be generally rectangular or any other desired shape, for example see FIGS. 49-54. Frame 110 is intended to support the decoupling element 170 and foam contacting portion 200 and connect the mask system 100 to the headgear 50, thereby securing the mask system 100 on the patient's face. Frame 110 connects to the headgear 50 by connecting portions 112, where rigidizers 90 removably connect to connecting portions 112 (e.g., see FIG. 7). Such a connection is described in U.S. patent application Ser. No. 12/219,852 (Guney), which is incorporated herein by reference in its entirety. Frame 110 may be at least partially constructed from a resilient material such as silicone, polycarbonate, polypropylene, nylon, or any other desired material.

2.3 Decoupling Element

Decoupling element 170 may be generally oval as shown in FIGS. 11 and 49-54 with orifice 175 adapted to align with opening in foam contacting portion 200. Decoupling element 170 may absorb some of the forces from the frame, headgear and tube by flexing and compressing (e.g., like a gusset or suspension system) so as to prevent misalignment of the foam contacting portion 200 with the nares of the patient. Decoupling element 170 may be formed from a flexible material such as silicone. Decoupling element 170 may be connected to frame 110 by an interference fit. Alternatively, decoupling element 170 may be permanently fixed or formed with the frame 110 by co-molding or glue. Decoupling element 170 may also be attached to the foam contacting portion. In one form, the foam contacting portion 200 is a layer of foam that is wrapped, connected, slid or otherwise positioned on a supporting structure.

In a further embodiment, the decoupling element 170 of the support structure may be the decoupling element disclosed in U.S. patent application Ser. No. 12/219,852 (Guney), which is incorporated herein by reference in its entirety. In an embodiment, the frame 110 of the mask system 100 may be the frame disclosed in U.S. patent application Ser. No. 12/219,852 (Guney).

The particularly soft mechanical properties of an exemplary foam (as disclosed in PCT Publication No. WO 2008/070929 (Veliss et al)) means that the foam contacting portion may be provided with support and reinforcement to perform its function with the nasal air passages. The frame 110 and decoupling element 170 may be suitable structures to provide this supporting mechanism, providing appropriate balance between shape and support for positioning the foam contacting portion 200, structural compliance and resilience for comfort on the nose (e.g., allow rotational, axial, and/or lateral movement to resist tube drag and headgear tension).

2.4 Headgear

Headgear 50 may include three main strap sections: top straps 60, back strap 70 and side straps 80. Top straps 60 may be placed over the top of the patient's head and may be one continuous piece of material or multiple pieces of material joined together by a buckle 95 as shown in FIGS. 1-3.

Back strap 70 may be placed around the back of the patient's head and may be one piece of continuous material or multiple pieces of material joined together by a buckle.

Top strap 60 and back strap 70 may be adjusted using hook and loop fasteners (such as Velcro™) or with the buckle 95. Buckle 95 may also have a lock that prevents the top strap 60 from loosening off. Such a buckle 95 with lock is described in U.S. Pat. No. 7,318,437 (Gunaratnam et al), which is incorporate herein by reference in its entirety.

Side straps 80 are generally positioned on the sides of the patient's face, from above or near the ear, passing under the eyes and ending at the nose of the patient. Side straps 80 may be reinforced with rigidizers 90 that may assist in supporting the mask system 100 in position. Rigidizers 90 may be attached to side straps at: the patient contacting side of side straps 80 (not shown), within side straps 80 by co-molding or other such technique (not shown), or on the exterior non-patient contacting side of side straps 80 (see FIGS. 1 and 3). Rigidizers 90 may be connected to side straps 80 by: gluing, stitching, co-molding, or any other suitable means.

Side straps 80 may also include cheek supports 85 that lie generally horizontally on the cheeks of the patient, generally at the cheek bone region, to better position the mask system 100 on the face of the user. Such an arrangement is shown in U.S. patent application Ser. No. 12/219,852 (Guney).

3. Air Delivery 3.1 Introduction

The mask system 100 may be connected to a supply of pressurized breathable gas to deliver therapy to the patient. The air delivery system 130 may include: an elbow 140 and a tube 150 as shown in FIGS. 1-3.

3.2 Elbow

Elbow 140 is generally an L-shaped, hollow cylinder and may be constructed of a generally rigid material such as polycarbonate or polypropylene. Elbow 140 may also include one or more vent holes 160 (see FIG. 3) to allow exhaust gases from the patient to expel into the atmosphere. Elbow 140 may also include a one way anti-asphyxia valve.

In a further embodiment, the elbow 140 may be the same as that disclosed in U.S. patent application Ser. No. 12/219,852 (Guney).

3.3 Tube

Tube 150 is generally a hollow, cylinder with a reinforcing member 155 (see FIGS. 1 and 3) integrally molded into tube 150. The reinforcing member 155 may include a generally helical shape so as to allow the tube 150 to flex without occluding. Tube 150 may be flexible, resilient and stretchable in a longitudinal direction.

Tube 150 may be constructed of a polymer or fabric, e.g., Hytrel™. Such a tube is disclosed in U.S. Provisional Patent Application No. 61/031,407 (Henry et al), filed Feb. 26, 2008, which is incorporated herein by reference in its entirety.

Tube 150 may connect to the elbow 140 so as to deliver breathable gas to the patient through the patient interface 10. The tube 150 may connect to elbow 140 by any reasonable means, such as a clip, interference fit, etc.

In a further embodiment, the tube 150 may be the same as that disclosed in U.S. patent application Ser. No. 12/219,852 (Guney).

In the illustrated forms of the invention, the mask system 100 of which the foam interfacing portion forms a part is generally configured under the nose of the patient. However, in other forms, the mask system 100 may be a nasal or full-face mask, or an oro-nasal mask. For example, in one form, a foam-based under-the-nose configuration may be combined with a gel, silicone or rubber portion, for example a silicone mouth cushion.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention. Also, the various embodiments described above may be implemented in conjunction with other embodiments, e.g., aspects of one embodiment may be combined with aspects of another embodiment to realize yet other embodiments. Further, each independent feature or component of any given assembly may constitute an additional embodiment. Furthermore, each individual component of any given assembly, one or more portions of an individual component of any given assembly, and various combinations of components from one or more embodiments may include one or more ornamental design features. In addition, while the invention has particular application to patients who suffer from OSA, it is to be appreciated that patients who suffer from other illnesses (e.g., congestive heart failure, diabetes, morbid obesity, stroke, bariatric surgery, etc.) can derive benefit from the above teachings. Moreover, the above teachings have applicability with patients and non-patients alike in non-medical applications.

What is claimed is:

1. A patient interface for delivering breathable gas to a patient, the patient interface comprising:
    a foam interfacing portion formed of foam and adapted to provide a nasal interface, the foam interfacing portion including an orifice adapted to be in fluid communication with both the patient's nares in use; and
    a positioning and stabilizing structure to support the foam interfacing portion in an operative position on the patient's face,
    wherein the foam interfacing portion is removably connected to the positioning and stabilizing structure, the foam interfacing portion being wrapped around at least a portion of the positioning and stabilizing structure such that an exterior surface of a bottom underside portion of the foam interfacing portion forms a concave shape extending from a first side of the at least a portion of the positioning and stabilizing structure to a second side of the at least a portion of the positioning and stabilizing structure opposite the first side, the exterior surface of the bottom underside portion of the foam interfacing portion being in direct contact with the positioning and stabilizing structure, and
    wherein the foam interfacing portion being secured in its wrapped position by one or more connectors.

2. A patient interface according to claim 1, wherein the positioning and stabilizing structure includes a frame, a decoupling element, and/or headgear.

3. A patient interface according to claim 2, wherein the positioning and stabilizing structure includes the decoupling element, and wherein the foam interfacing portion is provided to an exterior surface of the decoupling element.

4. A patient interface according to claim 2, wherein the positioning and stabilizing structure includes the frame and the decoupling element, and wherein the foam interfacing portion is wrapped around the frame and the decoupling element.

5. A patient interface according to claim 2, wherein the positioning and stabilizing structure includes the decoupling element, and wherein the decoupling element is formed from silicone.

6. A patient interface according to claim 2, wherein the foam interfacing portion is secured in position using existing structure on the decoupling element, frame, and/or headgear.

7. A patient interface according to claim 2, wherein the orifice is structured to align with an orifice provided to the frame and/or decoupling element.

8. A patient interface according to claim 2, wherein the positioning and stabilizing structure includes the frame, and wherein the foam interfacing portion covers substantially an entirety of the frame.

9. A patient interface according to claim 1, wherein the connectors include a male connector and a female connector.

10. A patient interface according to claim 9, wherein the foam interfacing portion includes the male connector and a frame and/or decoupling element includes the female connector.

11. A patient interface according to claim 1, wherein the exterior surface of the bottom underside portion of the foam interfacing portion has a first end at a first side of the foam interfacing portion and a second end at an opposite second side of the foam interfacing portion, and
    wherein the entire exterior surface from the first end to the second end is formed into the concave shape.

12. A patient interface according to claim 11, wherein an exterior surface on a topside patient-contacting portion of the foam interfacing portion has a convex shape that matches a curvature of the concave shape of the exterior surface of the bottom underside portion of the foam interfacing portion.

13. A patient interface according to claim 12, wherein the convex shape of the exterior surface of the topside patient-contacting portion of the foam interfacing portion is configured and positioned to directly contact under the patient's nose in use.

14. A patient interface according to claim 12, wherein a distance between the exterior surface of the bottom underside portion of the foam interfacing portion and the exterior surface of the topside patient-contacting portion of the foam interfacing portion is uniform from the first side of the foam interfacing portion to the second side of the foam interfacing portion.

15. A patient interface according to claim 1, wherein the connectors include a hook and loop arrangement.

16. A patient interface according to claim 1, wherein the connectors include a press stud arrangement.

17. A patient interface according to claim 1, wherein the connectors include a hook and loop material.

18. A patient interface according to claim 1, wherein the connectors include a clip arrangement.

19. A patient interface according to claim 1, wherein the orifice of the foam interfacing portion is D-shaped.

20. A patient interface according to claim 1, wherein the orifice of the foam interfacing portion includes a width of about 15-50 mm.

21. A patient interface according to claim 1, wherein the orifice of the foam interfacing portion includes a height of about 5-30 mm.

22. A patient interface according to claim 1, wherein the foam interfacing portion includes a thickness of about 0.5-50 mm.

23. A patient interface according to claim 1, wherein the foam interfacing portion includes a length of about 10-200 mm and a width of about 10-100 mm.

24. A patient interface according to claim 1, wherein the foam interfacing portion is structured to form a seal with the patient's nares.

25. A patient interface according to claim 1, wherein the exterior surface of the bottom underside portion of the foam interfacing portion substantially surrounds the at least a portion of the positioning and stabilizing structure.

26. A patient interface according to claim 1, wherein the positioning and stabilizing structure is flexible, compressible and/or movable to allow rotational, axial, and/or lateral movement of the foam interfacing portion.

27. A patient interface according to claim 1, wherein at least one of the one or more connectors is disposed on the exterior surface of the bottom underside portion of the foam interfacing portion.

28. A patient interface according to claim 1, wherein the concave shape substantially conforms to a shape of the at least a portion of the positioning and stabilizing structure.

29. A patient interface according to claim 1, wherein the foam is configured and positioned to directly contact under and around the patient's nose in use.

30. A patient interface according to claim 1, wherein the positioning and stabilizing structure includes a frame, and
wherein the positioning and stabilizing structure resists the application of tube drag and/or headgear tension to the foam interfacing portion.

31. A patient interface according to claim 1, wherein the foam interfacing portion is wrapped around the positioning and stabilizing structure such that an underside surface of the foam interfacing portion forms an arc shape around the at least a portion of the positioning and stabilizing structure.

32. A patient interface according to claim 1, wherein an entire underside surface of the foam interfacing portion is in contact with the positioning and stabilizing structure.

33. A patient interface according to claim 1, wherein the foam interfacing portion forms an inverted U-shape and the foam interfacing portion covers the at least a portion of the positioning and stabilizing structure.

34. A patient interface according to claim 1, wherein at least one of the one or more connectors is disposed on the exterior surface of the bottom underside portion of the foam interfacing portion, and
wherein the concave shape substantially conforms to a shape of the at least a portion of the positioning and stabilizing structure.

35. A patient interface according to claim 1, wherein the foam interfacing portion is wrapped around the positioning and stabilizing structure such that an underside surface of the foam interfacing portion forms an arc shape around the at least a portion of the positioning and stabilizing structure,
wherein an entire underside surface of the foam interfacing portion is in contact with the positioning and stabilizing structure,
wherein the exterior surface of the bottom underside portion of the foam interfacing portion has a first end at a first side of the foam interfacing portion and a second end at an opposite second side of the foam interfacing portion, the entire exterior surface from the first end to the second end being formed into the concave shape,
wherein an exterior surface on a topside patient-contacting portion of the foam interfacing portion has a convex shape that matches a curvature of the concave shape of the exterior surface of the bottom underside portion of the foam interfacing portion,
wherein the convex shape of the exterior surface of the topside patient-contacting portion of the foam interfacing portion is configured and positioned to directly contact under the patient's nose in use,
wherein a distance between the exterior surface of the bottom underside portion of the foam interfacing portion and the exterior surface of the topside patient-contacting portion of the foam interfacing portion is uniform from the first side of the foam interfacing portion to the second side of the foam interfacing portion,
wherein the foam interfacing portion forms an inverted U-shape and the foam interfacing portion covers the at least a portion of the positioning and stabilizing structure,
wherein at least one of the one or more connectors is disposed on the exterior surface of the bottom underside portion of the foam interfacing portion, and
wherein the concave shape substantially conforms to a shape of the at least a portion of the positioning and stabilizing structure.

* * * * *